(12) United States Patent
Wang et al.

(10) Patent No.: US 8,658,174 B2
(45) Date of Patent: *Feb. 25, 2014

(54) GLP/1/EXENDIN 4 IGG FC FUSION CONSTRUCTS FOR TREATMENT OF DIABETES

(75) Inventors: Qinghua Wang, Toronto (CA); Gerald J. Purd'homme, Toronto (CA)

(73) Assignee: Qinghua Wang, North York, NY (US)

( * ) Notice: Subject to any disclaimer, the term of this patent is extended or adjusted under 35 U.S.C. 154(b) by 1339 days.

This patent is subject to a terminal disclaimer.

(21) Appl. No.: 11/996,776

(22) PCT Filed: Jul. 27, 2006

(86) PCT No.: PCT/CA2006/001231
§ 371 (c)(1),
(2), (4) Date: Oct. 15, 2008

(87) PCT Pub. No.: WO2007/012188
PCT Pub. Date: Feb. 1, 2007

(65) Prior Publication Data
US 2009/0181912 A1    Jul. 16, 2009

Related U.S. Application Data

(60) Provisional application No. 60/595,689, filed on Jul. 27, 2005.

(51) Int. Cl.
*A61K 39/00* (2006.01)

(52) U.S. Cl.
USPC ...................................................... 424/134.1

(58) Field of Classification Search
None
See application file for complete search history.

(56) References Cited

U.S. PATENT DOCUMENTS

| 5,998,366 A | 12/1999 | Tobin et al. |
| 6,992,174 B2 | 1/2006 | Gillies et al. |
| 2009/0016968 A1 | 1/2009 | Wang et al. |

FOREIGN PATENT DOCUMENTS

| WO | WO 0164254 A2 | 9/2001 |
| WO | WO 0246227 | 6/2002 |
| WO | WO 0246227 A2 | 6/2002 |
| WO | WO 02057435 | 7/2002 |
| WO | WO 2005000892 | 1/2005 |
| WO | WO 2005023291 A2 | 3/2005 |
| WO | WO 2005060642 | 7/2005 |
| WO | WO 2005097175 | 10/2005 |

OTHER PUBLICATIONS

Carel, J., "Therapy to Prevent Type 1 Diabetes Mellitus", New England Journal of Medicine, Oct. 3, 2002, pp. 1115-1116, vol. 347.

Ogawa, N. et al., "Cure of Overt Diabetes in NOD Mice by Transient Treatment with Anti-Lymphocyte Serum and Exendin-4", Diabetes, 2004, pp. 1700-1705, vol. 53.
Keymeulen, B. et al., "Insulin Needs after CD3-Antibody Therapy in New-Onset Type 1 Diabetes", New England Journal of Medicine, Jun. 23, 2005, pp. 2598-2608, vol. 352.
Malendowicz L.K., "Effects of prolonged exendin-4 administration on entero-insular axis of normal and streptozotocin-induced diabetic rats", Int. J. Mol. Med. Jun. 2003, vol. 11, No. 6, p. 763-766.
Prud'homme G.J. et al., "Immunoinhibitory DNA vaccine protects against autoimmune diabetes through cDNA encoding a slective CTLA-4 (CD152) ligand", Hum. Gene Ther., Feb. 2002, 13(3):395-406.
Glinka, Y., "Regulatory cytokine production stimulated by DNA vaccination against an altered form of glutamic acid decarboxylase 65 in nonobese diabetic mice", J. Mol. Med., Mar. 2003, 81(3):175-184.
Malendowicz L.K., Effects of prolonged exendin-4 administration on entero-insular axis of normal and streptozotocin-induced diabetic rats. Int. J. Mol. Med. Jun. 2003, vol. 11, No. 6, p. 763-6.
Yu, Liping et al. Diabetes Prevention Trial 1. Prevalence of GAD and ICA512 (IA-2) Autoantibodies by Relationship to Proband. Annals of the New York Academy of Sciences, 2002, pp. 254-258, vol. 958.
Sia, Charles et al. Tolerance Induction and Endogenous Regeneration of Pancreatic β-Cells in Established Autoimmune Diabetes. The Review or Diabetic Studies, 2004, pp. 198-206, vol. 1 No. 4.
Sherry, Nicole A., et al. Exendin-4 Improves Reversal of Diabetesin NOD Mice Treated with Anti-CD3 Monoclonal Antibody by Enhancing Recovery of β-Cells. Endocrinology, 2007, pp. 5136-5144, vol. 148, No. 11.
Chang, Yigang et al. Intramuscular Administration of Expression Plasmids Encoding Interferon-gamma Receptor/IgG1 or IL-4/IgG1 Chimeric Proteins Protects from Autoimmunity. The Journal of Gene Medicine, 1999, pp. 415-423, vol. 1, Issue 6.
Hogarth Mark P. et al. Fc receptor-targeted therapies for the treatment of inflammation, cancer and beyond. Nature Reviews. vol. 11, Apr. 2012, p. 311-331.
Glaesner, Wolfgang et al., Engineering and characterization of the long-acting glucagon-like peptide-1 analogue LY2189265, and Fc fusion protein, Diabetes Metabolism Research and Reviews, 2010; vol. 26, pp. 287-296.
Jefferis, Roy et al., Interaction sites on human IgG-Fc for Fc•R: current models, Immunology Letters, 2002, vol. 82, pp. 57-65.
King, Leslie B. et al., Immunobiology of the immature B cell: plasticity in the B-cell antigen receptor-induced response fine tunes negative selection, Immunological Reviews, 2000, vol. 176, pp. 86-104.
Kumpel, B.M. et all, Section 1C: Assessment of the functional activity and IgG Fc receptor utilisation of 64 IgG Rh monoclonal antibodies. Coordinators report., Transfus Clin. Biol,, 2002, vol. 9, pp. 45-53.
Lee, Ai-Young et al., Insulin-induced Drug Eruptions and Reliability of Skin Tests, Acta Derm Venereol, 2002, vol. 82, pp. 114-117.
Liang, Yarning et al., Immunity against a therapeutic xenoprotein/Fc construct delivered by gene transfer is reduced through binding to the inhibitory reception Fc•RIIb, The Journal of Gene Medicine, 2011, vol. 13, pp. 470-477.
Melo, Marco E.F. et al., Gene Transfer of Ig-Fusion Proteins Into B Cells Prevents and Treats Autoimmune Diseases, The Journal of Immunology, 2002, vol. 168, pp. 4788-4795.

(Continued)

*Primary Examiner* — Gerald R Ewoldt
(74) *Attorney, Agent, or Firm* — Bereskin & Parr LLP; Micheline Gravelle; Carmela DeLuca

(57) ABSTRACT

The invention is a method and composition for the prevention and treatment of type I and type II diabetes in a subject. The composition comprises an IgG-Fc fusion protein where the fusion protein comprises GLP-1, mutant GLP-1, or exendin-4.

6 Claims, 11 Drawing Sheets

(56) References Cited

OTHER PUBLICATIONS

Prislovsky, Amanda et al., Rapid platelet turnover in WASP(−) mice correlates with increased ex vivo phagocytosis of opsonized WASP(−) platelets, Experimental Hematology, 2008, vol. 36, pp. 609-623.

Takai, Toshiyuki, Fc Receptors and Their Role in Immune Regulation and Autoimmunity, Journal of Clinical Immunology, Jan. 2005, vol. 25, No. 1, pp. 1-18.

Uray, Katalin et al., Synthesis and receptor binding of IgG1 peptides derived from the IgG Fc region, Journal of Molecular Recognition, 2004, vol. 17, pp. 95-105.

Wang, Q. et al., Glucagon-like peptide-1 regulates proliferation and apoptosis via activation of protein kinase B in pancreatic INS-1 beta cells, Diabetologia, 2004, vol. 47, pp. 478-487.

Wang, Q. et au., Glucagon-like peptide-1 treatment delays the onset of diabetes in 8 week-old db/db mice, Diabetologia, 2002, vol. 45, pp. 1263-1273.

SEQUENCE LISTING

<160> NUMBER OF SEQ ID NOS: 20

<210> SEQ ID NO 1
<211> LENGTH: 32
<212> TYPE: PRT
<213> ORGANISM: Homo Sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Asn His
            20                  25                  30

<210> SEQ ID NO 2
<211> LENGTH: 41
<212> TYPE: PRT
<213> ORGANISM: Helicoderma Suspectum

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Asn His
        35                  40

<210> SEQ ID NO 3
<211> LENGTH: 249
<212> TYPE: PRT
<213> ORGANISM: Mus Musculus

<400> SEQUENCE: 3

Pro Ser Glu Thr Val Thr Cys Asn Val Ala His Pro Ala Ser Ser Thr
1               5                   10                  15

Lys Val Asp Lys Lys Ile Val Pro Arg Asp Cys Gly Cys Lys Pro Cys
            20                  25                  30

Ile Cys Thr Val Pro Glu Val Ser Val Phe Ile Phe Pro Pro Lys
            35                  40                  45

Pro Lys Asp Val Leu Thr Ile Thr Leu Thr Pro Lys Val Thr Cys Val
 50                  55                  60

Val Val Asp Ile Ser Lys Asp Asp Pro Glu Val Gln Phe Ser Trp Phe
 65                  70                  75                  80

Val Asp Asp Val Glu Val His Thr Ala Gln Thr Gln Pro Arg Glu Glu
                 85                  90                  95

Gln Phe Asn Ser Thr Phe Arg Ser Val Ser Glu Leu Pro Ile Met His
            100                 105                 110

Gln Asp Trp Leu Asn Gly Lys Glu Phe Lys Cys Arg Val Asn Ser Ala
        115                 120                 125

Ala Phe Pro Ala Pro Ile Glu Lys Thr Ile Ser Lys Thr Lys Gly Arg
    130                 135                 140

Pro Lys Ala Pro Gln Val Tyr Thr Ile Pro Pro Lys Glu Gln Met
145                 150                 155                 160

Ala Lys Asp Lys Val Ser Leu Thr Cys Met Ile Thr Asp Phe Phe Pro
                165                 170                 175

Glu Asp Ile Thr Val Glu Trp Gln Trp Asn Gly Gln Pro Ala Glu Asn
            180                 185                 190

Tyr Lys Asn Thr Gln Pro Ile Met Asn Thr Asn Gly Ser Tyr Phe Val
        195                 200                 205

Tyr Ser Lys Leu Asn Val Gln Lys Ser Asn Trp Glu Ala Gly Asn Thr
    210                 215                 220

Phe Thr Cys Ser Val Leu His Glu Gly Leu His Asn His His Thr Glu
225                 230                 235                 240

Lys Ser Leu Ser His Ser Pro Gly Lys
                245

<210> SEQ ID NO 4
<211> LENGTH: 21
<212> TYPE: PRT
<213> ORGANISM: Homo Sapiens

<400> SEQUENCE: 4

Met Glu Thr Asp Thr Leu Leu Leu Trp Val Leu Leu Leu Trp Val Pro
 1               5                  10                  15

Gly Ser Thr Gly Asp
             20

<210> SEQ ID NO 5
<211> LENGTH: 417
<212> TYPE: PRT
<213> ORGANISM: Homo sapiens

<400> SEQUENCE: 5

Met Lys Thr Glu Arg Pro Arg Pro Asn Thr Phe Ile Ile Arg Cys Leu
 1               5                  10                  15

Gln Trp Thr Thr Val Ile Glu Arg Thr Phe His Val Glu Thr Pro Glu
             20                  25                  30

Glu Arg Glu Glu Trp Thr Thr Ala Ile Gln Thr Val Ala Asp Gly Leu
         35                  40                  45

Lys Lys Gln Glu Glu Glu Met Asp Phe Arg Ser Gly Ser Pro Ser
     50                  55                  60

Asp Asn Ser Gly Ala Glu Glu Met Glu Val Ser Leu Ala Lys Pro Lys
 65                  70                  75                  80

```
His Arg Val Thr Met Asn Glu Phe Glu Tyr Leu Lys Leu Leu Gly Lys
                 85                  90                  95

Gly Thr Phe Gly Lys Val Ile Leu Val Lys Glu Lys Ala Thr Ala Tyr
            100                 105                 110

Tyr Ala Met Lys Ile Leu Lys Lys Glu Val Ile Val Ala Lys Asp Glu
        115                 120                 125

Val Ala His Thr Leu Thr Glu Asn Arg Val Gln Gln Asn Ser Arg His
    130                 135                 140

Pro Phe Leu Thr Arg Leu Lys Tyr Ser Phe Gln Thr His Asp Arg Leu
145                 150                 155                 160

Cys Phe Val Met Glu Tyr Ala Asn Gly Gly Leu Phe Phe His Leu
                165                 170                 175

Ser Arg Glu Arg Val Phe Ala Glu Asp Arg Ala Arg Phe Tyr Gly Ala
            180                 185                 190

Glu Ile Val Ser Ala Leu Asp Tyr Leu His Ser Glu Lys Asn Val Val
        195                 200                 205

Tyr Arg Asp Leu Lys Leu Glu Asn Leu Met Leu Asp Lys Asp Gly His
    210                 215                 220

Ile Lys Ile Thr Asp Phe Gly Leu Cys Lys Glu Gly Ile Lys Asp Gly
225                 230                 235                 240

Ala Thr Met Lys Thr Phe Cys Gly Thr Pro Glu Tyr Leu Ala Pro Glu
                245                 250                 255

Val Leu Glu Asp Asn Asp Tyr Gly Arg Ala Val Asp Trp Trp Gly Leu
            260                 265                 270

Gly Val Val Met Tyr Glu Met Met Cys Gly Arg Leu Pro Phe Tyr Asn
        275                 280                 285

Gln Asp His Glu Lys Leu Phe Glu Leu Ile Leu Met Glu Glu Ile Arg
    290                 295                 300

Phe Pro Arg Thr Leu Gly Pro Glu Ala Lys Ser Leu Leu Ser Gly Leu
305                 310                 315                 320

Leu Lys Lys Asp Pro Lys Gln Arg Leu Gly Gly Ser Glu Asp Ala
                325                 330                 335

Lys Glu Ile Met Gln His Arg Phe Phe Thr Gly Ile Val Trp Gln His
                340                 345                 350

Val Tyr Glu Lys Lys Leu Ser Pro Pro Phe Lys Pro Gln Val Thr Ser
        355                 360                 365

Glu Thr Asp Thr Arg Tyr Phe Asp Glu Glu Phe Thr Ala Gln Met Ile
    370                 375                 380

Thr Ile Thr Pro Pro Asp Gln Asp Asp Ser Met Glu Cys Val Asp Ser
385                 390                 395                 400

Glu Arg Arg Pro His Phe Pro Gln Phe Ser Tyr Ser Pro Ser Ala Thr
                405                 410                 415

Ala

<210> SEQ ID NO 6
<211> LENGTH: 424
<212> TYPE: PRT
<213> ORGANISM: Homo sapiens

<400> SEQUENCE: 6

Met Ser Asp Ser Lys Cys Asp Ser Gln Phe Tyr Ser Val Gln Val Ala
1               5                   10                  15

Asp Ser Thr Phe Thr Val Leu Lys Arg Tyr Gln Gln Leu Lys Pro Ile
            20                  25                  30

Gly Ser Gly Ala Gln Gly Ile Val Cys Ala Ala Phe Asp Thr Val Leu
```

```
                35                  40                  45
Gly Ile Asn Val Ala Val Lys Lys Leu Ser Arg Pro Phe Gln Asn Gln
 50                  55                  60

Thr His Ala Lys Arg Ala Tyr Arg Glu Leu Val Leu Leu Lys Cys Val
 65                  70                  75                  80

Asn His Lys Asn Ile Ile Ser Leu Leu Asn Val Phe Thr Pro Gln Lys
                 85                  90                  95

Thr Leu Glu Glu Phe Gln Asp Val Tyr Leu Val Met Glu Leu Met Asp
            100                 105                 110

Ala Asn Leu Cys Gln Val Ile His Met Glu Leu Asp His Glu Arg Met
            115                 120                 125

Ser Tyr Leu Leu Tyr Gln Met Leu Cys Gly Ile Lys His Leu His Ser
130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Cys Thr Asn Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Ile
            195                 200                 205

Trp Ser Val Gly Cys Ile Met Gly Glu Leu Val Lys Gly Cys Val Ile
210                 215                 220

Phe Gln Gly Thr Asp His Ile Asp Gln Trp Asn Lys Val Ile Glu Gln
225                 230                 235                 240

Leu Gly Thr Pro Ser Ala Glu Phe Met Lys Lys Leu Gln Pro Thr Val
                245                 250                 255

Arg Asn Tyr Val Glu Asn Arg Pro Lys Tyr Pro Gly Ile Lys Phe Glu
            260                 265                 270

Glu Leu Phe Pro Asp Trp Ile Phe Pro Ser Glu Ser Glu Arg Asp Lys
            275                 280                 285

Ile Lys Thr Ser Gln Ala Arg Asp Leu Leu Ser Lys Met Leu Val Ile
290                 295                 300

Asp Pro Asp Lys Arg Ile Ser Val Asp Glu Ala Leu Arg His Pro Tyr
305                 310                 315                 320

Ile Thr Val Trp Tyr Asp Pro Ala Glu Ala Glu Ala Pro Pro Pro Gln
                325                 330                 335

Ile Tyr Asp Ala Gln Leu Glu Glu Arg Glu His Ala Ile Glu Glu Trp
            340                 345                 350

Lys Glu Leu Ile Tyr Lys Glu Val Met Asp Trp Glu Glu Arg Ser Lys
            355                 360                 365

Asn Gly Val Val Lys Asp Gln Pro Ser Asp Ala Ala Val Ser Ser Asn
370                 375                 380

Ala Thr Pro Ser Gln Ser Ser Ser Ile Asn Asp Ile Ser Ser Met Ser
385                 390                 395                 400

Thr Glu Gln Thr Leu Ala Ser Asp Thr Asp Ser Ser Leu Asp Ala Ser
                405                 410                 415

Thr Gly Pro Leu Glu Gly Cys Arg
            420

<210> SEQ ID NO 7
<211> LENGTH: 278
<212> TYPE: PRT
<213> ORGANISM: Homo sapiens
```

<400> SEQUENCE: 7

```
Met Glu Asn Thr Glu Asn Ser Val Asp Ser Lys Ser Ile Lys Asn Leu
1               5                   10                  15

Glu Pro Lys Ile Ile His Gly Ser Glu Ser Met Asp Ser Gly Met Ser
            20                  25                  30

Trp Asp Thr Gly Tyr Lys Met Asp Tyr Pro Glu Met Gly Leu Cys Ile
        35                  40                  45

Ile Ile Asn Asn Lys Asn Phe His Lys Ser Thr Gly Met Thr Ser Arg
50                  55                  60

Ser Gly Thr Asp Val Asp Ala Ala Asn Leu Arg Glu Thr Phe Arg Asn
65                  70                  75                  80

Leu Lys Tyr Glu Val Arg Asn Lys Asn Asp Leu Thr Arg Glu Glu Ile
                85                  90                  95

Val Glu Leu Met Arg Asp Val Ser Lys Glu Asp His Ser Lys Arg Ser
            100                 105                 110

Ser Phe Val Cys Val Leu Leu Ser His Gly Glu Glu Gly Ile Ile Phe
        115                 120                 125

Gly Thr Asn Gly Pro Val Asp Leu Lys Lys Ile Thr Asn Phe Phe Arg
    130                 135                 140

Gly Asp Arg Cys Arg Ser Leu Thr Gly Lys Pro Lys Leu Phe Ile Ile
145                 150                 155                 160

Gln Ala Cys Arg Gly Thr Glu Leu Asp Cys Gly Ile Glu Thr Asp Ser
                165                 170                 175

Gly Val Asp Asp Asp Met Ala Cys His Lys Ile Pro Val Asp Ala Asp
            180                 185                 190

Phe Leu Tyr Ala Tyr Ser Thr Ala Pro Gly Tyr Tyr Ser Trp Arg Asn
        195                 200                 205

Ser Lys Asp Gly Ser Trp Phe Ile Gln Ser Leu Cys Ala Met Leu Lys
    210                 215                 220

Gln Tyr Ala Asp Lys Leu Glu Phe Met His Ile Leu Thr Arg Val Asn
225                 230                 235                 240

Arg Lys Val Ala Thr Glu Phe Glu Ser Phe Ser Phe Asp Ala Thr Phe
                245                 250                 255

His Ala Lys Lys Gln Ile Pro Cys Ile Val Ser Met Leu Thr Lys Glu
            260                 265                 270

Leu Tyr Phe Tyr His Leu
        275
```

<210> SEQ ID NO 8
<211> LENGTH: 902
<212> TYPE: DNA
<213> ORGANISM: Homo sapiens

<400> SEQUENCE: 8

```
gagcgcaaat gttgtgtcga gtgcccaccg tgcccaggta agccagccca ggcctcgccc      60
tccagctcaa ggcgggacag gtgccctaga gtagcctgca tccagggaca ggccccagct    120
gggtgctgac acgtccacct ccatctcttc ctcagcacca cctgtggcag gaccgtcagt    180
cttcctcttc cccccaaaac ccaaggacac cctcatgatc tcccggaccc ctgaggtcac    240
gtgcgtggtg gtggacgtga gccacgaaga ccccgaggtc cagttcaact ggtacgtgga    300
cggcgtggag gtgcataatg ccaagacaaa gccacgggag gagcagttca acagcacgtt    360
ccgtgtggtc agcgtcctca ccgttgtgca ccaggactgg ctgaacggca aggagtacaa    420
gtgcaaggtc tccaacaaag gcctcccagc ccccatcgag aaaaccatct ccaaaaccaa    480
```

```
aggtgggacc cgcggggtat gagggccaca tggacagagg ccggctcggc ccaccctctg      540
ccctgggagt gaccgctgtg ccaacctctg tccctacagg gcagcccga gaaccacagg      600 tgtacaccct gccccatcc cgggaggaga tgaccaagaa ccaggtcagc ctgacctgcc      660
tggtcaaagg cttctacccc agcgacatcg ccgtggagtg ggagagcaat gggcagccgg      720
agaacaacta caagaccaca cctcccatgc tggactccga cggctccttc ttcctctaca      780
gcaagctcac cgtggacaag agcaggtggc agcaggggaa cgtcttctca tgctccgtga      840
tgcatgaggc tctgcacaac cactacacgc agaagagcct ctccctgtct ccgggtaaat      900
ga                                                                    902
```

```
<210> SEQ ID NO 9
<211> LENGTH: 228
<212> TYPE: PRT
<213> ORGANISM: Homo sapiens

<400> SEQUENCE: 9

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225
```

```
<210> SEQ ID NO 10
<211> LENGTH: 57
<212> TYPE: DNA
<213> ORGANISM: Homo sapiens

<400> SEQUENCE: 10
gtgctctggg tgttcttctt tgtgatcctc accctcagca acagctccca ctgctcc       57
```

<210> SEQ ID NO 11
<211> LENGTH: 80
<212> TYPE: DNA
<213> ORGANISM: Homo Sapiens

<400> SEQUENCE: 11
ccggatatcg ccaccatgga gacagacaca ctcctgctat gggtactgct gctctgggtt    60
ccaggttcca ctggtgacca                                                80

<210> SEQ ID NO 12
<211> LENGTH: 23
<212> TYPE: DNA
<213> ORGANISM: Homo Sapiens

<400> SEQUENCE: 12
tgctgaaggg acctttacca gtg                                            23

<210> SEQ ID NO 13
<211> LENGTH: 96
<212> TYPE: DNA
<213> ORGANISM: Mus Musculus

<400> SEQUENCE: 13
ccggatatcg ccaccatgga gacagacaca ctcctgctat gggtactgct gctctgggtt    60
ccaggttcca ctggtgaccc cagcgagacc gtcacc                              96

<210> SEQ ID NO 14
<211> LENGTH: 37
<212> TYPE: DNA
<213> ORGANISM: Mus Musculus

<400> SEQUENCE: 14
cgcggatccc tatcatttac caggagagtg ggagagg                             37

<210> SEQ ID NO 15
<211> LENGTH: 103
<212> TYPE: DNA
<213> ORGANISM: Homo Sapiens

<400> SEQUENCE: 15
ccggatatcg ccaccatgga gacagacaca ctcctgctat gggtactgct gctctgggtt    60
ccaggttcca ctggtgacca tgctgaaggg acctttacca gtg                      103

<210> SEQ ID NO 16
<211> LENGTH: 37
<212> TYPE: DNA
<213> ORGANISM: Homo Sapiens

<400> SEQUENCE: 16
cgcggatccc tatcatttac caggagagtg ggagagg                             37

<210> SEQ ID NO 17
<211> LENGTH: 96
<212> TYPE: DNA
<213> ORGANISM: Mus Musculus

<400> SEQUENCE: 17
ccggatatcg ccaccatgga gacagacaca ctcctgctat gggtactgct gctctgggtt    60
ccaggttcca ctggtgaccc cagcgagacc gtcacc                              96

<210> SEQ ID NO 18
<211> LENGTH: 37

```
<212> TYPE: DNA
<213> ORGANISM: Mus Musculus

<400> SEQUENCE: 18
cgcggatccc tatcatttac caggagagtg ggagagg                              37

<210> SEQ ID NO 19
<211> LENGTH: 36
<212> TYPE: DNA
<213> ORGANISM: Homo Sapiens

<400> SEQUENCE: 19
aaggatatcg atcgcaaatg ttgtgtcgag tgccca                               36

<210> SEQ ID NO 20
<211> LENGTH: 32
<212> TYPE: DNA
<213> ORGANISM: Homo Sapiens

<400> SEQUENCE: 20
cgtaagcttc atttacccgg agacagggag ag                                   32
```

GLP/1/EXENDIN 4 IGG FC FUSION CONSTRUCTS FOR TREATMENT OF DIABETES

INCORPORATION OF SEQUENCE LISTING

A computer readable form of the Sequence Listing "12960-4_SequenceListing.txt" (18,287 bytes), submitted via EFS-WEB and created on Mar. 5, 2013, is herein incorporated by reference.

FIELD OF THE INVENTION

The invention is directed to the prevention and treatment of diabetes. In particular, the invention provides a composition and method for the treatment of type I and type II diabetes in mammals. The composition comprises GLP-1 or Ex4 fusion proteins.

BACKGROUND OF THE INVENTION

Diabetes mellitus is a leading cause of death and affects over 20 million people in North America alone and about 200 million worldwide (American Diabetes Association: www.diabetes.org and Canadian Diabetes Association: www.diabetes.ca; World Health Organization: http://www.who.int/diabetes). The two major forms of the disease are type I and type II diabetes. Both are characterized by a progressive decrease in beta-cell mass and beta-cell function.

Type I diabetes (also called juvenile diabetes) is a complex T-cell dependent autoimmune disease (Juneja and Palmer, Autoimmunity. 1999; 29(1):65-83) that typically develops at a young age. Type I diabetes results from the autoimmune destruction of islet beta-cells with consequent insulin deficiency and dependence on exogenous insulin treatment. The focal infiltration of the endocrine pancreas by mononuclear cells and a strikingly decreased functional beta-cell mass constitute the histopathological hallmarks of the disease at diagnosis, but there is a marked inter-individual variability in terms of the extent of these lesions. The beta-cell apoptosis occurs as a result of autoimmune destruction involving T cell infiltration of the islets of Langerhans (Lee et al., Mol Genet Metab. 2004; 83(1-2):82-92; Mandrup-Poulsen, Biochem Pharmacol. 2003; 66(8):1433-1440; Sesti, Ann Med. 2002; 34(6):444-450; Mathis et al., Nature. 2001; 414(6865):792-798). To study the underlying molecular mechanism of diabetes, animal models have been developed. For example, streptozotocin (STZ)-induced insulin-deficient rats or mice mimic the T-cell mediated inflammation and destruction of islet beta-cells seen in diabetes patients. The non-obese diabetic (NOD) mouse is another model of autoimmune diabetes where islet-antigen reactive T cells infiltrate the islets of Langerhans and kill islet beta cells, and/or initiate an inflammatory process that results in islet beta cell death (Anderson and Bluestone, Annu Rev Immunol. 2005; 23:447-485).

Insulin therapy is a major intervention for the treatment of type I diabetes. Pancreatic islet transplantation is an effective therapy (Shapiro et al., N Engl J. Med. 2000; 343(4):230-238) but is limited largely by the limited resources of human islet. In addition, immune-suppressors need to be used in the islets-transplanted patients for life. Though insulin therapy is used for most patients with type I diabetes, insulin is not a cure as it is difficult to maintain blood glucose levels within a narrow physiological range, and it does not prevent the progression of the disease nor the development of severe diabetic complications.

Type II diabetes is a polygenic disorder typically diagnosed in adulthood and is characterized by three major abnormalities that contribute to the development of hyperglycemia: 1) peripheral insulin resistance, 2) excessive hepatic glucose production, and 3) pancreatic beta-cell dysfunction. Insulin resistance is defined as the reduced response to insulin in peripheral tissues, mainly the skeletal muscle cells, leading to impaired glucose transport into these tissues (Kahn and Goldfine, J Diabetes Complications. 1993; 7(2):92-105; Weyer et al., J Clin Invest. 1999; 104(6):787-794). Insulin resistance can also occur in the liver where insulin is unable to efficiently suppress hepatic glucose production (Kahn and Goldfine, 3 Diabetes Complications. 1993; 7(2):92-105; Lam et al., Am J Physiol Endocrinol Metab. 2002; 283(4):E682-E691). Furthermore, excessive pancreatic glucagon secretion is also a major contributor to the disproportionate over-production of hepatic glucose (Unger and Orci, Arch Intern Med. 1977; 137(4):482-491). As a result of insulin resistance, the body's demand for insulin is increased. In the early stages of insulin resistance, the blood glucose levels can still be maintained within a normal range via a compensatory mechanism increasing insulin output that involves increased beta-cell mass in the pancreas (Bonner-Weir, Trends Endocrinol Metab. 2000; 11(9):375-378; Bonner-Weir, Endocrinology. 2000; 141(6):1926-1929). Numerous studies indicate that insulin resistance on its own is not sufficient to trigger the onset of diabetes, if the beta-cell compensatory capacity is maintained (Weyer et al., Diabetes. 1999; 48(11):2197-2203). However, in the long term and when insulin resistance becomes severe, the increased demand for insulin leads to beta-cell exhaustion, decreased insulin production, and the development of fasting hyperglycaemia and overt diabetes (DeFronzo, Diabetes. 1988; 37(6):667-687; Kahn et al., J Nutr. 2001; 131(2):354S-360S; Weyer et al., J Clin Invest. 1999; 104(6):787-794). The obese insulin resistance db/db mouse is a severe animal model of type II diabetes. These mice are deficient in leptin signaling (Herberg and Coleman, Metabolism. 1977; 26(1):59-99; Chen et al., Cell. 1996; 84(3):491-495).

Conventional treatments for type II diabetes include diet and exercise as well as pharmacological interventions with sulphonylureas, metformin and insulin. These treatments generally fail to prevent the long-term decline in glycemic control and the beta-cell dysfunction in most patients (Matthews et al., Diabet Med. 1998; 15(4):297-303; Turner et al., JAMA. 1999; 281(21):2005-2012). Clinical management of type II diabetes using stepwise approaches also eventually fails to sustain glycemic control where, for most patients, there is a an unavoidable progression from diet and exercise to pharmacotherapy with a single agent, to combination therapy and finally to insulin (Turner et al., JAMA. 1999; 281(21): 2005-2012; Gerich, Eur J Clin Invest. 2002; 32 Suppl 3:46-53). The ineffectiveness of these therapies in preventing either the progression of type II diabetes or the long-term complications associated with this disease may be a consequence of the focus of these approaches on the symptoms (i.e. hyperglycemia) rather than the cause of type II diabetes (Gerich, Eur J Clin Invest. 2002; 32 Suppl 3:46-53).

Glucagon-like peptide-1 (7-36)-amide (GLP-1) is an insulinotropic hormone (Brubaker and Drucker, Endocrinology. 2004; 145(6):2653-2659; Perfetti and Merkel, Eur J Endocrinol. 2000; 143(6):717-725; Hoist, Gastroenterology. 1994; 107(6):1848-1855; Holst and Gromada, Am J Physiol Endocrinol Metab. 2004; 287(2):E199-E206) that is secreted from intestinal L-cells in response to nutrient ingestion and promotes nutrient absorption via regulation of islet hormone secretion (Drucker, Diabetes. 1998; 47(2):159-169). GLP-1 binds to the GLP-1 receptor (GLP-1R), a G-protein coupled receptor (GPCR). GLP-1R is expressed mainly by pancreatic beta-cells, and to some extent by cells of other tissues (lungs, heart, kidney, GI tract and brain), and is coupled to the cyclic AMP (cAMP) second messenger pathway to initiate its biological actions (Drucker, Endocrinology. 2001; 142(2):521-527; Brubaker and Drucker, Endocrinology. 2004; 145(6): 2653-2659), (Brubaker and Drucker, Receptors Channels. 2002; 8(3-4):179-188; Brubaker and Drucker, Endocrinology. 2004; 145(6):2653-2659; Thorens, Proc Natl Acad Sci USA. 1992; 89(18):8641-8645) protein kinase A (PKA) and the Epac family of cAMP-regulated guanine nucleotide exchange factors (cAMPGEFs) (Miura and Matsui, Toxicol Appl Pharmacol. 2006; Holz, Horm Metab Res. 2004; 36(11-12):787-794). Activation of other protein kinases including Akt (protein kinase B) and MAPK (Mitogen-Activated Protein Kinases (MAPK)) (Brubaker and Drucker, Endocrinology. 2004; 145(6):2653-2659; Wang and Brubaker, Diabetologia. 2002; 45(9):1263-1273; Wang et al., Diabetologia. 2004; 47(3):478-487) is also found to be important in mediating GLP-1 action in promoting beta-cell growth and inhibiting apoptosis.

GLP-1 enhances pancreatic islet beta-cell proliferation and inhibits beta-cell apoptosis in a glucose-dependent fashion (Nauck et al., Horm Metab Res. 1997; 29(9):411-416; Nauck, Horm Metab Res. 2004; 36(11-12):852-858; Drucker, Diabetes. 1998; 47(2):159-169). GLP-1 also augments insulin secretion and lowers blood glucose in rodents as well as in humans in both type I diabetes (Gutniak et al., Diabetes Care. 1994; 17(9):1039-1044) and type II diabetes (Nauck et al., Diabetes. 1997; 105(4):187-195; Todd et al., Eur J Clin Invest. 1997; 27(6):533-536; Nathan et al., Diabetes Care. 1992; 15(2):270-276). In animals models of type II diabetes, GLP-1 or its long-acting potent analogue exendin-4 (Ex4) treatment prevented onset of diabetes (Wang and Brubaker, Diabetologia. 2002; 45(9):1263-1273; Tourrel et al., Diabetes. 2002; 51(5):1443-1452) by enhancing beta-cell growth and inhibiting apoptosis (Wang and Brubaker, Diabetologia. 2002; 45(9):1263-1273; Wang, Endocrinology Rounds. 2004; 3(7); Wang et al., Diabetologia. 2004; 47(3):478-487; Tourrel et al., Diabetes. 2002; 51(5):1443-1452). GLP-1 has demonstrated clinical efficacy in type II diabetes (Meier and Nauck, Diabetes Metab Res Rev. 2005; 21(2):91-117). Studies demonstrated that in insulin-secreting beta-cells, the apoptosis and necrosis induced by cytokines could be significantly blocked by GLP-1 or exendin-4 (Ex4) (Saldeen, Endocrinology. 2000; 141(6):2003-2010; Li et al., Diabetologia. 2005). Treatment with GLP-1/Ex4 stimulated beta-cell neogenesis in STZ-treated newborn rats resulting in persistently improved glucose homeostasis at an adult age (Tourrel et al., Diabetes. 2001; 50(7):1562-1570). Furthermore, administration of GLP-1/Ex4, combined with immunosuppression by polyclonal anti-T cell antibody, induced remission in 88% of diabetic NOD mice (Ogawa et al., Diabetes. 2004; 53(7):1700-1705).

U.S. Pat. No. 6,899,883 and U.S. Pat. No. 6,989,148 disclose methods of treating type I diabetes using insulin and glucagon-like peptide 1(7-37) or glucagon-like peptide 1(7-36) amide. Native GLP-1 has a short circulating half-life ($t_{1/2}$<2 min) that results mainly from rapid enzymatic inactivation including dipeptidyl-peptidase IV (DPP-IV) (Drucker, Diabetes. 1998; 47(2):159-169), and/or renal clearance (Montrose-Rafizadeh et al., Endocrinology. 1999; 140(3): 1132-1140). Therefore, continuous subcutaneous infusion by pump is necessary to maintain GLP-1 action in vivo (Toft-Nielsen et al., Diabetes Care. 1999; 22(7):1137-1143). A DPPIV inhibitor can increase the half-life of GLP-1, DPPIV also inactivates several other peptide hormones and some chemokines (Meier and Nauck, Diabetes Metab Res Rev. 2005; 21(2):91-117), and its inhibition may lead to adverse reactions. In this respect, efforts have been made to develop pharmaceutical long-acting degradation-resistant GLP-1 mimetic peptides. Human GLP-1 analogues with amino acid substitutions (Ahren and Schmitz, Horm Metab Res. 2004; 36(11-12):867-876; Green et al., Curr Pharm Des. 2004; 10(29):3651-3662) and/or N-terminal modifications including fatty acylated (Chang et al., Diabetes. 2003; 52(7):1786-1791) and N-acetylated (Liu et al., Cell Biol Int. 2004; 28(1): 69-73) modifications exhibit prolonged circulating $t_{1/2}$, and potently reduce glycemic excursion in diabetic subjects (Chang et al., Diabetes. 2003; 52(7):1786-1791). Ex4, a reptilian peptide with high sequence homology to mammalian GLP-1 is a potent GLP-1R agonist (Fineman et al., Diabetes Care. 2003; 26(8):2370-2377). Furthermore, albumin protein-conjugated GLP-1 (Albugon) also has the anti-diabetic and other beneficial activities of GLP-1 along with a prolonged half-life (Kim et al., Diabetes. 2003; 52(3):751-759).

Although DPP-IV-resistant GLP-1R agonists as well as Ex4 appear to be promising therapeutic drug candidates for the treatment of diabetes, these peptides require once- or twice-daily injections and/or combination therapies with oral diabetic medications. The substantially prolonged half-life of GLP-1-albumin fusion proteins, or GLP-1 fusion $IgG_4$ fusion proteins such as those described in WO 02/46227 or WO 05/000892, is likely the result of reduced renal clearance due to the larger size. However, in vitro studies have shown that a fusion protein displays a lower potency (Kim et al., Diabetes. 2003; 52(3):751-759). This has fostered complementary efforts to generate more potent longer-acting agents with sustained efficacy in vivo.

Thus, there still remains a need to develop effective treatment strategies that target the molecular mechanisms underlying type I and type II diabetes rather than the consequences. Intervention with therapies that target both the beta-cell dysfunction and insulin resistance are desirable. Therefore, a therapy that promotes beta-cell growth and also protects from beta-cell death is necessary for effective treatment of this disease.

SUMMARY OF THE INVENTION

The invention is a method and compositions for the prevention and treatment of type I and type II diabetes. The composition of the invention comprises a novel fusion protein. The fusion protein comprises GLP-1 molecule or its analogue(s) or fragments fused with IgG heavy chain constant (Fc) regions. In aspects the IgG is any mouse IgG such as but not limited to $IgG_1$. In further aspects, the IgG is human and may be selected from $IgG_1$, $IgG_2$ or $IgG_3$. The fusion protein of the invention is herein referred to as "GLP-1/IgG-Fc". In other aspects of the invention, the fusion protein comprises Ex4/IgG-Fc where the IgG may be mouse or human as described herein.

The compositions of the invention are effective for the treatment of both type I and type II diabetes in a subject. As such, the invention provides a method for the treatment of type I and/or type II diabetes in a subject, where the fusion proteins are administered to a subject in need of.

The invention also provides a novel method of production of the fusion proteins of the invention, GLP-1/$IgG_1$-Fc and Ex4/IgG-Fc fusion proteins using mammalian expression and bacterial culture systems. In both of these systems, the cell clones are generated to produce fusion proteins including GLP-1/$IgG_1$-Fc and GLP-1/$IgG_2$-Fc as well as therapeutically effective mutant forms resistant to DPPIV degradation such as but not limited to GLP-1A8G/IgG-Fc (alanine at the position 8 is replaced by glycine) and Ex4/IgG-Fc.

The bivalent GLP-1/IgG-Fc fusion protein of the invention possess unique features: 1) increased circulating $t_{1/2}$; 2) higher avidity and potency, 3) minimized immunogenicity and 4) easy purification involving one-step strategy for large-scale production. The composition of the invention may be provided to a subject in need of such in a variety of modes. In one embodiment one or two intramuscular injections of GLP-1/IgG-Fc and/or GLP-1A8G/IgG-Fc and/or or Ex4/IgG-Fc vectors achieved similar effects as that by two weeks of daily intraperitoneal injections of the Ex4.

According to an aspect of the present invention is a GLP-1 fusion protein that provides glycemic control in a subject.

According to an aspect of the present invention is a GLP-1 fusion protein that controls blood glucose concentrations in a subject.

According to an aspect of the present invention is a GLP-1 fusion protein that increases beta-cell proliferation and/or reduces beta-cell apoptosis thus enhances beta-cell mass in a subject.

According to an aspect of the present invention the fusion protein of the invention increases insulin release and glucose tolerance in the subject and also reduces fasting blood glucose levels in a subject.

According to an aspect of the present invention is a fusion protein comprising GLP-1 polypeptide or an analogue or mutant thereof or a fragment thereof and an IgG polypeptide.

According to an aspect of the present invention is a heterologous fusion protein comprising a GLP-1 polypeptide or variant thereof fused to an IgG polypeptide, wherein said IgG is not IgG4.

According to an aspect of the present invention the IgG is mouse.

According to an aspect of the present invention the IgG is mouse IgG1.

According to an aspect of the present invention the IgG is human.

According to an aspect of the present invention the IgG is human IgG1, IgG2 or IgG3.

According to an aspect of the present invention the IgG is human IgG2.

According to an aspect of the present invention the GLP-1 polypeptide is selected from the group consisting of GLP-1(7-37)OH, GLP-1(7-36)amide-1, a DPPIV resistant GLP-1 and fragments and variants thereof.

According to an aspect of the present invention the DPPIV resistant GLP-1 is GLP-1A8G.

According to an aspect of the present invention the variant comprises a polypeptide from about 70% to about 95% sequence identity with GLP-1 of Sequence ID NO. 1.

According to an aspect of the present invention the IgG the fragment comprises at least 5 amino acids up to about 250 amino acids.

According to an aspect of the present invention the IgG comprises an Fc portion of the IgG or a fragment or variant of the Fc portion.

According to an aspect of the present invention there is provided a cDNA encoding a the heterologous fusion protein.

According to an aspect of the present invention there is provided a vector comprising the cDNA of the heterologous fusion protein.

According to an aspect of the present invention there is provided a host cell transformed with the vector comprising the cDNA of the heterologous fusion protein.

According to an aspect of the present invention is a pharmaceutical composition comprising the heterologous fusion protein or the vector comprising the cDNA of the heterologous fusion protein in a pharmaceutically acceptable carrier.

According to an aspect of the present invention the pharmaceutical composition is for the treatment of type I and type II diabetes.

According to an aspect of the present invention the pharmaceutical composition is administered by a method selected from the group consisting of topical, oral, aerosol, intraperitoneal injection, intravenous injection and intramuscular injection.

According to an aspect of the present invention is a pharmaceutical composition for the treatment of type I and type II diabetes in a subject, said composition comprising a heterologous fusion protein comprising a GLP-1 polypeptide or variant or active fragment thereof fused to an IgG polypeptide.

According to an aspect of the present invention there is provided a method of treating type I and/or type II diabetes in a subject, the method comprising the administration of a therapeutically effective amount of the heterologous fusion protein or the composition or the vector.

According to an aspect of the present invention there is provided a use of a heterologous fusion protein for a medicament in the treatment of prevention of Type I and/or Type II diabetes in a subject.

According to an aspect of the present invention there is provided a heterologous fusion protein comprising an exendin-4 polypeptide or variant or fragment thereof fused to an IgG polypeptide.

According to an aspect of the present invention the IgG is selected from the group consisting of human IgG1, IgG2, IgG3 and IgG4.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

DESCRIPTION OF THE FIGURES

The present invention will be further understood from the following description with reference to the Figures, in which.

DETAILED DESCRIPTION OF THE PREFERRED EMBODIMENTS

Figure 1:
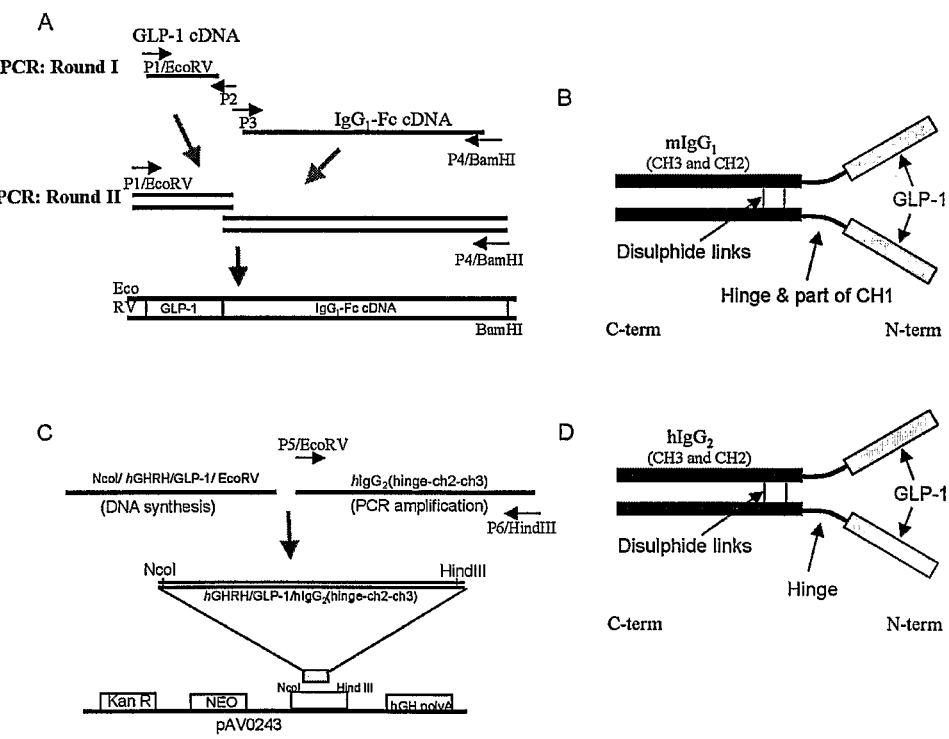
FIG. 1 construction of GLP-1/IgG-Fc-encoding plasmid. 1A, a cDNA encoding a GLP-1/mIgG1-Fc fusion protein was inserted between the Bam HI and Eco RV sites of the vector. A schematic representation of the secreted GLP-1/IgG-Fc fusion protein consisting of the active GLP-1 molecule (7-37) and the IgG-Fc encompassing the mouse IgG1 constant heavy-chain (part of CH1, hinge, CH2 and CH3) is shown in 1B. 1C, the cDNA encoding the fusion protein hGHRH/hGLP-1 was chemically synthesized, ligated to a PCR-amplified cDNA fragment encoding human IgG2 FC (hinge-ch2-ch3) and inserted into the NcoI and Hind III sites of the pAV0243 vector to generate GLP-1/hIgG-Fc/pAV0243. A schematic representation of the secretable GLP-1/hIgG-Fc fusion protein consisting of the active GLP-1 molecule (7-37) and the IgG-Fc encompassing the human IgG2 constant heavy-chain (hinge, CH2 and CH3) is shown in 1D. These proteins are secreted as homodimers upon expression. The cDNAs encoding a GLP-1A8G-IgG-Fc or Ex4/IgG-Fc fusion proteins were generated using site-directed mutagenesis. Similar strategy was used to generate a Ex4/IgG-Fc cDNA and cloned into pAV0243.

The invention provides compositions and methods for prevention and treatment of diabetes in a subject. The composition comprises a fusion protein that helps to regulate blood glucose levels. When administered in an effective amount to a subject, the compositions of the invention prevent the onset of diabetes such that beta-cell proliferation or neogenesis occurs. Proliferation refers to one beta-cell dividing into two beta-cells. Neogenesis refers to the production of totally new beta-cells from a progenitor cell or a stem cell. The compositions of the invention also reduce beta-cell apoptosis in the subject. The increased proliferation, neogenesis and reduced apoptosis provide for increased beta-cell mass. Furthermore, the insulin secretion from the beta-cells is increased by the compositions of the fusion proteins of the invention. The cyclic AMP (cAMP) and its coupled second messenger pathway(s) are activated by the compositions of the invention comprising the novel fusion proteins. Protein kinase (Akt1 and/or MAPK) expression in the beta-cell is increased by the fusion protein. The fusion protein also decreases caspase-3 activation. The effective amount of the compositions of the fusion proteins increases insulin release and glucose tolerance in the subject.

In one embodiment, the compositions and methods of the invention prolong the circulating $t_{1/2}$ of GLP-1 and enhance its potency. This is done by the provision of a fusion protein comprising active GLP-1 and IgG heavy chain constant regions (GLP-1/IgG-Fc). The GLP-1 peptide in aspects is native or is DPP-IV (Dipeptidyl Peptidase IV) resistant. The IgG may be mouse or human. In aspects, a mouse IgG may be $IgG_1$. A human IgG may be selected from $IgG_1$, $IgG_2$ and $IgG_3$. The GLP-1 polypeptide may be human or mouse sequence as they are identical. The GLP-1 polypeptide may be a variant fragment of a variant or fragment of the native sequence. The GLP-1 polypeptide may be GLP-1(7-37)OH or GLP-1(7-36)amide.

In another embodiment, the fusion protein of the invention comprises an Ex4 polypeptide a fragment of Ex4 or a variant or fragment of a variant thereof and IgG fragment (IgG-Fc).

The invention also provides vectors encoding secretable fusion proteins of the invention including but not limited to: active GLP-1 and mouse $IgG_1$-Fc cDNAs or GLP-1 human $IgG_2$-Fc cDNAs for mammalian expression of bivalent GLP-1 peptide; and active Ex-4-IgG cDNAs. One of skill in the art could readily prepare any desired GLP-1 or Ex4 sequence in a vector as is described herein in the examples or similar methods. The biological properties and effectiveness of the recombinant human chimeric GLP-1 fusion protein, GLP-1/IgG-Fc, was demonstrated using a combination of in vitro cell line studies and by a gene therapy approach by intramuscular gene transfer expression of the fusion proteins to type I and type II diabetic mouse models in vivo. This gene therapy approach proved effective in a murine model of severe type I and type II diabetes. Electroporation was used because it increased gene transfer and may prove useful in large animals and humans, where intramuscular gene transfer is less efficient than in rodents. Together, this invention provides a novel approaches for the treatment and prevention of type I and type II diabetes using protein and gene therapy techniques in mammalian subjects.

The fusion protein of the invention may be a GLP-1 or Ex4 fragment having a sequence that shares at least 60% sequence identity or more to a GLP-1 polypeptide or at least 60% or more sequence identity to an Ex4 polypeptide. In aspects, the sequence identity may be at least 70%, 80%, 90% or 95% or more sequence identity to known forms of GLP-1, and this includes analogues, derivatives thereof and fragments thereof. Such sequences are disclosed for example in U.S. Pat. No. 6,268,343 (the disclosure of which is incorporated herein by reference in its entirety). The invention includes the use of all the aforementioned compounds for prevention and treatment of diabetes, such as type I and type II diabetes patients. The invention also includes use of all the aforementioned compounds for preparation of a medicament for prevention and treatment of diabetes, such as type I and type II diabetes. The invention also includes a pharmaceutical composition, such as a prophylactic composition, for all the aforementioned uses.

The construction of fusion proteins combining GLP-1 with an IgG-Fc molecule forms a new molecule that possess enhanced GLP-1 actions and advantages of the IgG-Fc molecule i.e. increased ligand avidity and immunological tolerance. The invention provides fusion proteins combining derivatives of GLP-1 molecule including DPP-IV resistant form such as GLP-1A8G with an IgG-Fc molecule to form a new molecule that possess enhanced GLP-1 actions and advantages of IgG-Fc molecule as described. Similarly, fusion proteins combining GLP-1 receptor agonist (i.e. Ex4) with an IgG-Fc molecule to form new molecules that possess potent GLP-1-like actions and advantages of IgG-Fc molecule were also generated.

Changes which result in production of a chemically equivalent or chemically similar amino acid sequence are included within the scope of the invention. IgG-Fc-fused polypeptides sharing sequence identity to GLP-1 or Ex4 are within the scope of the present invention and may be readily tested to ensure that they are suitable for use in the methods of the invention. U.S. Pat. No. 6,268,343 (incorporated by reference in its entirety), describes a number of GLP-1 derivatives and variants. Variants of the polypeptides of the invention may occur naturally, for example, by mutation, or may be made, for example, with polypeptide engineering techniques such as site directed mutagenesis, which are well known in the art for substitution of amino acids. For example, a hydrophobic residue, such as glycine can be substituted for another hydrophobic residue such as alanine. An alanine residue may be substituted with a more hydrophobic residue such as leucine, valine or isoleucine. A negatively charged amino acid such as aspartic acid may be substituted for glutamic acid. A positively charged amino acid such as lysine may be substituted for another positively charged amino acid such as arginine.

Therefore, the invention encompasses IgG-Fc-fused polypeptides having conservative changes or substitutions in amino acid sequences. Conservative substitutions insert one or more amino acids, which have similar chemical properties as the replaced amino acids. The invention includes sequences where conservative substitutions are made that do not destroy compound activity. IgG-Fc-fused polypeptides comprising one or more D-amino acids are contemplated within the invention. Also contemplated are polypeptides where one or more amino acids are acetylated at the N-terminus. Those with skill in the art recognize that a variety of techniques are available for constructing polypeptide mimetics with the same or similar desired compound activity as the corresponding polypeptide compound of the invention but with more favorable activity than the polypeptide with respect to solubility, stability, and/or susceptibility to hydrolysis and proteolysis. See, for example, Morgan and Gainor, Ann. Rep. Med. Chem., 24:243-252 (1989). Examples of polypeptide mimetics are described in U.S. Pat. No. 5,643,873. Other patents describing how to make and use mimetics include, for example in, U.S. Pat. Nos. 5,786,322, 5,767,075, 5,763,571, 5,753,226, 5,683,983, 5,677,280, 5,672,584, 5,668,110, 5,654,276, 5,643,873 are all incorporated herein by reference in their entirety. Mimetics of the polypeptides of the invention may also be made according to other techniques known in the art. For example, by treating an IgG-Fc-fused polypeptide of the invention with an agent that chemically alters a side group by converting a hydrogen group to another group such as a hydroxyl or amino group. Mimetics preferably include sequences that are either entirely made of amino acids or sequences that are hybrids including amino acids and modified amino acids or other organic molecules. The invention also includes hybrid and IgG-Fc-fused polypeptides, for example where a nucleotide sequence is combined with a second sequence.

The invention also includes IgG-Fc-fused polypeptide fragments of the IgG-Fc-fused polypeptides of the invention that may be used to confer compound activity if the fragments retain activity. The invention also includes IgG-Fc-fused polypeptides fragments of the IgG-Fc-fused polypeptides of the invention which may be used as a research tool to characterize the polypeptide or its activity. Such polypeptides preferably consist of at least 5 amino acids. In preferred embodiments, they may consist of 6 to 10, 11 to 15, 16 to 25, 26 to 50, 51 to 75, 76 to 100 or 101 to 250 amino acids. Fragments may include sequences with one or more amino acids removed, for example, C-terminus amino acids in a compound sequence.

The activity of the compound fusion protein is increased or decreased by carrying out selective site-directed mutagenesis. A DNA plasmid or expression vector containing the nucleic acid molecule or a nucleic acid molecule having sequence identity is preferably used for these studies using the U.S.E. (Unique site elimination) mutagenesis kit from Pharmacia Biotech or other mutagenesis kits that are commercially available, or using PCR. Once the mutation is created and confirmed by DNA sequence analysis, the mutant fusion protein is expressed using an expression system and its activity is monitored.

The invention also includes fusion proteins which have sequence identity at least about: >20%, >25%, >28%, >30%, >35%, >40%, >50%, >60%, >70%, >80% or >90% more preferably at least about >95%, >99% or >99.5%, to a sequence of the invention (or a partial sequence thereof). Modified fusion proteins molecules are discussed below. Preferably about: 1, 2, 3, 4, 5, 6 to 10, 10 to 25, 26 to 50 or 51 to 100, or 101 to 250 nucleotides or amino acids are modified. Identity is calculated according to methods known in the art. Sequence identity is most preferably assessed by the BLAST version 2.1 program advanced search (parameters as above). BLAST is a series of programs that are available online at http://www.ncbi.nlm.nih.gov/BLAST. The advanced blast search (http://www.ncbi.nlm.nih.gov/blast/blast.cgi?Jform=1) is set to default parameters. (ie Matrix BLOSUM62; Gap existence cost 11; Per residue gap cost 1; Lambda ratio 0.85 default). References to BLAST searches are: Altschul, S. F., Gish, W., Miller, W., Myers, E.W. & Lipman, D. J. (1990) "Basic local alignment search tool." J. Mol. Biol. 215:403_410; Gish, W. & States, D. J. (1993) "Identification of protein coding regions by database similarity search." Nature Genet. 3:266_272; Madden, T. L., Tatusov, R. L. & Zhang, 3. (1996) "Applications of network BLAST server" Meth. Enzymol. 266:131_141; Altschul, S. F., Madden, T. L., Schäffer, A. A., Zhang, J., Zhang, Z., Miller, W. & Lipman, D. J. (1997) "Gapped BLAST and PSI_BLAST: a new generation of protein database search programs." Nucleic Acids Res. 25:3389_3402; and Zhang, J. & Madden, T. L. (1997) "PowerBLAST: A new network BLAST application for interactive or automated sequence analysis and annotation." Genome Res. 7:649_656.

The invention encompasses fusion proteins with mutations that cause an amino acid change in a portion of the fusion protein not involved in providing activity or an amino acid change in a portion of the fusion protein involved in providing activity so that the mutation increases or decreases the activity of the fusion protein. In aspects of the invention, the IgG-Fc portion of the fusion protein may also be modified by techniques well known to those skilled in the art to alter (increase or decrease) the level of immunogenicity and effector function as disclosed in WO 05/000892 (incorporated herein by reference in its entirety).

The fusion proteins of the invention are useful used alone, but may also be combined with other components such as a carrier in a pharmaceutical composition. The fusion proteins of the invention may be combined, i.e. more than one type may be administered to a subject, such as a human or animal, in soluble form to prevent or treat diabetes.

The pharmaceutical compositions can be administered to humans or animals by a variety of methods including, but not restricted to topical administration, oral administration, aerosol administration, intratracheal instillation, intraperitoneal injection, intravenous injection, intramuscular injection and gene therapy approach. Dosages to be administered depend on patient needs, on the desired effect and on the chosen route of administration. An example of a dosage for humans would be 2 nmol/kg of body weight or between about 0.02 to 100 nmol/kg of body weight. When gene therapy is used, a concentration of DNA for injection into humans would be 1 µg/kg of body weight or between 0.1 to 100 µg/kg of body weight. Fusion proteins may be introduced into cells using in vivo liposome or viral delivery vehicles. The numerous types of delivery vehicles suitable for use with the invention are well known to those skilled in the art. The compositions may be administered daily, weekly or as advised by a physician for as long as is required.

The pharmaceutical compositions can be prepared by known methods for the preparation of pharmaceutically acceptable compositions which can be administered to patients, and such that an effective quantity of the nucleic acid or polypeptide molecule is combined in a mixture with a pharmaceutically acceptable vehicle. Suitable vehicles are described, for example in Remington's Pharmaceutical Sciences (Remington's Pharmaceutical Sciences, Mack Publishing Company, Easton, Pa., USA). On this basis, the pharmaceutical compositions could include an active compound or substance, such as a compound nucleic acid, polypeptide molecule or fusion protein, in association with one or more pharmaceutically acceptable vehicles or diluents, and contained in buffered solutions with a suitable pH and isoosmotic with the physiological fluids. The methods of combining the active molecules with the vehicles or combining them with diluents is well known to those skilled in the art. The composition could include a targeting agent for the transport of the active compound to specified sites within tissue.

Proteins having sequence identity to the receptor for GLP-1 (or Ex4) may be tested to demonstrate that they are suitable for use in the methods of the invention. Small organic molecules are also tested. The invention includes compounds which are identified with the screening methods of the invention and which are suitable for methods and uses of the invention and in pharmaceutical compositions of the invention. In a preferred embodiment, the invention includes an assay for evaluating whether a candidate compound is capable of increasing cAMP generation, Akt-1 or MAPK expression or activity or decreasing caspase-3 expression or activity, by culturing cells (preferably beta-cells) in the presence of at least one compound whose ability to modulate (inhibit or activate) expression activity is sought to be determined and thereafter monitoring the cells for either an increase or decrease in the level of Akt-1 or MAPK expression or activity or decreasing caspase-3 expression or activity.

A receptor binding assay is the preferred method to evaluate the specificity of a compound for the cell membrane receptor, as all signaling transducing events are initiated from this ligand-receptor binding. If a candidate compound binds to the receptor (for example, as identified with a gel-shift mobility assay using cross-linking technique, or a competitive receptor binding assay), this binding indicates that the compound is suitable for use in the subsequent steps of the invention. Receptor activation assays are used to further determine the suitability of a candidate compound for the methods of the invention. For example, cAMP determination can be used to evaluate the receptor activation (GLP-1 receptor is GPCR). In addition, an Akt kinase assay can further show the activation of Akt. In the initial screens, when there are large numbers of compound candidates, a receptor binding assay can be used. Compounds that bind to the receptor are preferably subjected to cAMP determination, and finally an Akt kinase assay. Small organic molecules may also be tested as candidate compounds for their suitability for use in the methods of the invention. To this end, cAMP determination is optionally used to screen for GPCR binding and activation. As per the rationale described above, Akt kinase assay, or MAPK assay is optionally used to evaluate the cellular effectivity of the compounds.

To validate both screened peptide and organic molecule compounds, beta-cell mass analysis can be performed in the pre-diabetic animal models after treatment of the animal with the compounds for a longer period (i.e. 2-12 weeks). To this end, an additional insulin-release assay can also performed using an insulin radioimmunoassay kit (Linco Research, St. Louis, Mo.). These experimental approaches confirm the growth effects of the screened compounds on the beta-cells. To validate both screened peptide and organic molecule compounds, beta-cell mass analysis can be performed in the pre-diabetic animal model after treatment of the animal with the compounds for a longer period (i.e. 2-12 weeks). To this end, an additional Insulin-release assay can also performed using an insulin radioimmunoassay kit (Linco Research, St. Louis, Mo.). These experimental approaches confirm the growth effects of the screened compounds on the beta-cells. To validate screened vectors, the DNA plasmids can be administered to pre-diabetic animal models through gene transfer. The administration can be repeated every two months or six months or every year or as deemed necessary.

The compositions of the invention may be used in conjunction with any other known agents for treatment for type I and/or type II diabetes, such as for example with the use of diabetes medicaments and insulins. Diabetic medicaments may include for example Actos, Amaryl, avandia, DiaBeta, Diabinese, Dymelor, Glucophage, Glucophage XR, Glucotrol, Glucotrol XL, Glucovance, glynase, PresTab, Glyset, Micronase, Orinase, Pandin, Precose, Starlix and Tolinase. Suitable insulins include for example Aspart, Insulin Glargine (Lantus), Lente, Lispro (Humalog), NPH and Ultralente.

A subject for which the present invention is suitable is any subject in need of such treatment which is one that is at risk for developing diabetes, a subject newly diagnosed with diabetes or a subject already diagnosed with diabetes. The invention is relevant towards the treatment and/or prevention of type I and type II diabetes as described herein. For example, such subjects may be an obese person or a person with a genetic history of diabetes who has not yet developed diabetes or, who has newly diagnosed or diagnosed as diabetes. The World Health Organization (WHO) defines obesity by reference to body mass index (BMI). This is a measure derived from dividing body weight in kg by the square of height in meters. A BMI between 18.5 and 25 is normal weight. An individual is overweight with a BMI between 25 and 30. An obese subject is defined as a subject with a BMI equal to or greater than 30. The subject may also be a person whose blood glucose is higher than average for that person's age and weight (normal blood glucose may be routinely determined from medical reference sources), although not high enough that the person is diagnosed diabetic. The subject may also be a person with a genetic history of diabetes who has not yet developed diabetes. Diabetes is diagnosed when the blood sugar levels are higher than an accepted normal range. According to ADA (American Diabetes Association) and CDA (Canadian Diabetes Association) standards, diabetes onset occurs when a subject has a fasting blood glucose level over 7.0 mmol/L, or a random (anytime of day) sugar that is greater than 11.1 mmol/L. Once diagnosed, any effort/means made to the patient, in order to combat the hyperglycemia, is treatment, rather than prevention. Some people, although not diabetic, (e.g. obese people, whose excess weight is usually associated with insulin resistance) have poor health and a higher risk of development of type II diabetes. To reduce or minimize their risk of developing type II diabetes, the compounds of the invention are administered to prevent and/or treat type II diabetes. Furthermore, the compounds of the invention are administered to prevent and/or treat a subject with type I diabetes. Type I diabetes patient refers to a subject who usually has genetic predisposition or, who has insulitis beta-cell injury or, who has "pre"-diabetes with loss of first phase of insulin response, or a person who has been newly diagnosed diabetes. In newly diagnosed type I diabetes patients, as a result of the immune system attacking and destroying the insulin-producing islet beta-cells, their pancreas produce little or no insulin.

This invention also provides novel plasmids encoding a fusion protein comprising human GLP-1 (7-37) and human or mouse IgG-Fc using overlap PCR (Polymerase Chain Reaction) (FIG. 1). The IgG-Fc region contained the mouse $IgG_1$ constant heavy-chain (part of CH1, hinge, CH2 and CH3). In an embodiment of the invention, the IgG-Fc region may be human $IgG_2$ constant heavy-chain (hinge, $CH_2$ and $CH_3$). Also shown is a method to incorporate a leading sequence into a vector that allowing the fusion protein to be express and secreted to an extracellular medium environment. As shown, an IgK secretion leader peptide sequence is fused with the GLP-1 sequence that directs the secretion of the synthesized peptide into the medium. In an embodiment of the invention, a human Growth Hormone Releasing Hormone (GHRH) leader peptide sequence (gtg ctc tgg gtg ttc ttc ttt gtg atc ctc acc ctc agc aac agc tcc cac tgc tcc) is fused with the GLP-1 sequence that directs the secretion of the synthesized peptide into the medium. In each case, this strategy ensured the generation of a GLP-1 fusion with an active histidine residue at the N-terminus of the fusion protein after cleavage of the secretion leader sequence peptide during the process of secretion. A schematic representation of the secreted GLP-1/IgG-Fc fusion proteins is shown in FIG. 1. This approach circumvents the short circulating half-life of GLP-1 since Fc fusion proteins are secreted as homodimers that possess longer circulating half-life and higher efficacy due to higher ligand avidity; (2) enhance the peptide potency since most GPCR are pre-formed in dimers at the cell surface; and 3) facilitate the purification, which can be achieved by one-step purification using Protein G sepharose.

Figure 2:
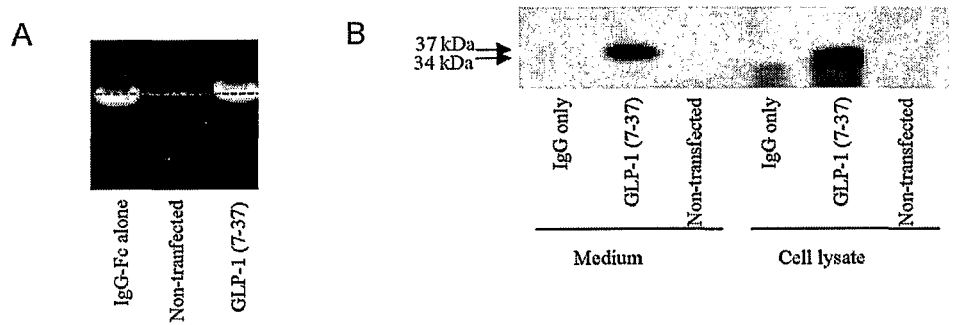
FIG. 2 shows the expression and detection of IgG-Fc fusion protein in COS-7 cells. COS-7 cells were transfected with the IgG-Fc fusion constructs and total RNA was isolated 48-h post transfection. 2A shows the RT-PCR products on a 1% agarose gel and visualized using ethidium bromide. 2B shows the fusion proteins purified using Protein G sepharose and resolved by SDS-PAGE and transferred to a nitrocellulose membrane. The membrane was probed with anti-mouse antibody (1:5000) and visualized by ECL.

Expression of the novel vectors of the fusion protein was demonstrated using a mammalian expression system. To assess the capacity of the vectors in terms of expression and secretion of the GLP-1/IgG-Fc fusion proteins, constructs were transiently transfected into COS-7 cells. Forty-eight hours after transfection, to evaluate the expression of the fusion constructs, total RNA from the transfected cells was prepared and expression was analyzed using RT-PCR. Transcripts for the GLP-1/IgG-Fc fusion constructs and IgG-Fc control constructs were detected using the gene specific primers (FIG. 2a). No transcripts were detected in non-transfected samples.

The lysates and medium from the transfected COS-7 cells were also analyzed for expression of the fusion proteins by Western blotting using anti-mouse IgG antibodies. As shown in FIG. 2b, Fc fusion proteins were detected in both the medium and cell lysates. The fusion proteins could be detected by RT-PCR (Reverse Transcription Polymerase Chain Reaction), western blotting or GLP-1 radio-immunoassay (RIA). Detection of the fusion proteins both in the conditioned media and the cell lysates indicates that the fusion proteins were synthesized and secreted from the mammalian cells.

Figure 3:
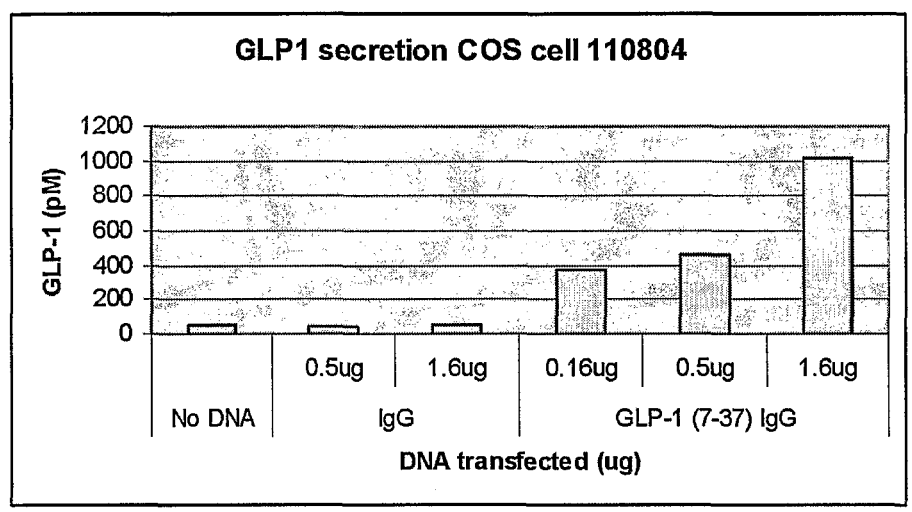
FIG. 3 is a graph showing the secretion of GLP-1 from transfected COS-7 cells. COS-7 cells were plated in 12-well plates and transfected with varying amounts of GLP-1/IgG-Fc or IgG-Fc only plasmids. The medium was collected 48-h post transfection and 150 μL of the medium was used to detect GLP-1 by RIA.
Figure 4A:
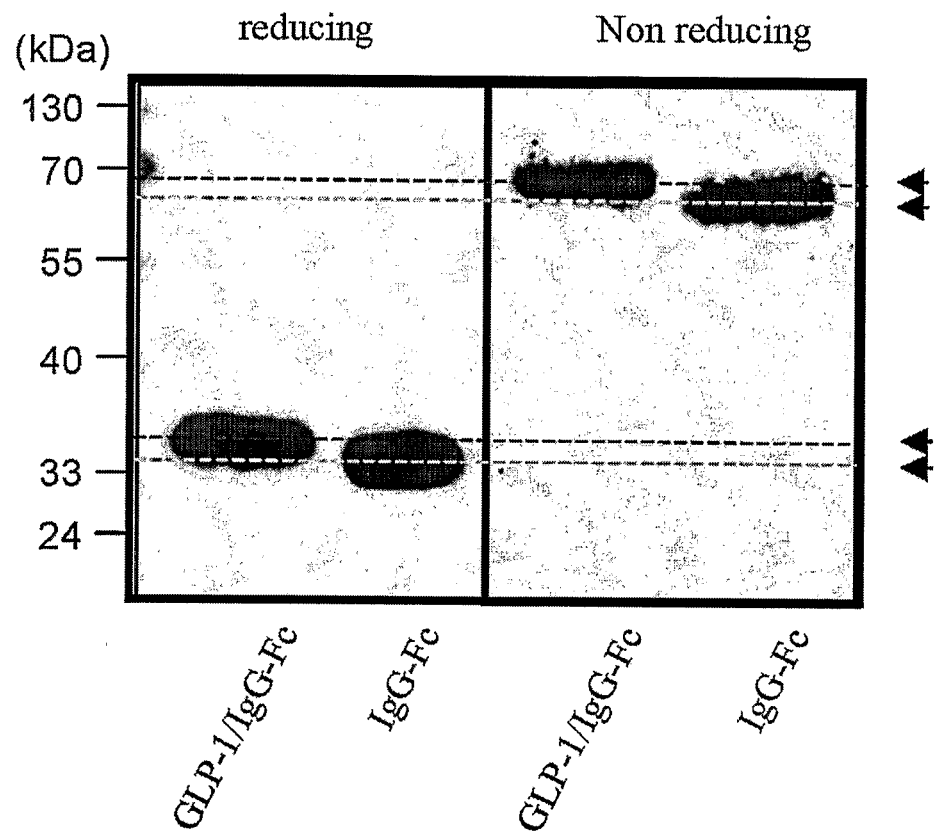
FIG. 4A shows large scale expression of IgG-Fc fusion proteins in COS-7 cells. COS-7 cells were plated in 150 mm dishes and transfected with 80 μg of DNA the following day. Forty-eight hours after transfection, the medium was collected and fusion proteins purified by incubating with 1 mL of Protein G Sepharose overnight. The beads were washed and the purified proteins were eluted by adding 1 mL of 0.1M glycine (pH 2.7). The elution was repeated and the fractions were pooled. 30 μL fractions were analyzed by SDS-PAGE under reducing or non-reducing conditions as indicated and staining with Coomassie Blue.

The identity of the GLP-1 fusion protein was further confirmed by a GLP-1 radioimmunoassay (RIA), which allows for detection of all forms of GLP-1. COS-7 cells were transiently transfected with increasing amounts of GLP-1/IgG-Fc or IgG-Fc-only plasmids and media were collected 48 hours following transfection. The medium was used in GLP-1 RIAs to detect total GLP-1. While no GLP-1 was detected in medium from non-transfected or IgG-Fc-only transfected COS-7 cells, GLP-1 was detected in a DNA-dose dependent manner in the medium collected from GLP-1/IgG-Fc-transfected cells (FIG. 3). One-step purification (Jungbauer et al., 3 Chromatogr. 1989; 476:257-268) from 50 ml culture medium (2-day static culture when seeding at ~1.25×10$^5$ cells/ml) using Protein G sepharose could yield ~300 µg fusion as estimated by Coomassie Blue-stained SDS-PAGE of which detected a ~35 kDa or ~70 kDa (FIG. 4) band under reducing or non-reducing conditions respectively, indicating that bivalent GLP-1/IgG-Fc fusion protein exists in native conditions. The fusion proteins displayed capacity to stimulate insulin secretion in a glucose-dependent manner (FIG. 1D) and cAMP generation (FIG. 1E) in INS-1 cells.

Using assay methods, the efficacy of fusion proteins GLP-1/IgG-Fc (its DPP-IV resistant mutant form and Ex-4-IgG-Fc) were tested and demonstrated. Assay methods included the receptor binding assay, cAMP (Adenosine 3',5'-cyclic monophosphate) assay and insulin stimulation assay using beta-cells that have capacity to secret insulin under proper stimulatory conditions. Other assays may be also applied to study the beta-cell proliferation by the fusion proteins or to determine signaling cascade after activation of GLP-1 receptor by GLP-1/IgG-Fc fusion proteins its derivates described. These assays are proliferation assay (3H-thymidine incorporation), Akt kinase activity assay, MAPK assay and apoptotic assay using caspase-3 or other caspase-family members.

The techniques for in vivo expression of GLP-1/IgG-Fc molecules are described herein. An example is given that in mouse and in pig, the fusion proteins can be persistently expressed in in vivo via intramuscularly injection. The local electroporation technique may additionally be used because it greatly increases gene transfer that might be required in large animals and humans. In this study, the animals were monitored for bodyweight and fasting blood glucose weekly, and saphenous vein bleedings were collected prior to injection and 2 weeks and 12 weeks after the first injection for measurement of fasting insulin and glucagon levels. Expression of the GLP-1/IgG-Fc protein was evaluated by measuring plasma levels of active GLP-1 using a GLP-1 Elisa kit (Linco). As shown, 2 weeks after the first injection the plasma GLP-1 levels were significantly elevated in mice injected with GLP-1/IgG-Fc compared to those mice injected with IgG-Fc vectors. These elevated levels declined by 16 weeks post-injection, but were still higher than that of control mice (FIG. 8A).

In one embodiment, GLP-1/IgG-Fc, GLP-1A8G/IgG-Fc and Ex4/IgG-Fc are shown to be effective for the prevention and treatment of type I and type II diabetes, using for example, 1) the pre-diabetic db/db mouse as a model of type II diabetes and 2) the streptozotocin (STZ)-induced type I insulin deficient mouse as a model of type I diabetes. Db/db mice lack a functional leptin receptor and spontaneously develop obesity, hyperinsulinemia, and glucose intolerance at 4-6 week of age, progressing to frank diabetes by 8 weeks of age. These mice have thus been used extensively and are recognized as a model for type II diabetes. STZ-induced insulin deficient mice are generated by the administration of multiple low doses of the drug streptozotocin (STZ) to specifically destroy the beta-cells involving T-cells mediated infiltration. These mice have thus been used extensively and are recognized as an animal model that is mimics type I diabetes in subjects. Other mouse diabetic models currently available and can be used in the present invention is the high fat diet-induced insulin resistant mouse model; these mice develop obesity and insulin resistance as a result of excessive ingestion of fat which leads to over-deposition of fat in the body and associated with pathological transforms, insulin resistance and glucose intolerance. Another animal model is the non-obese diabetic (NOD) mouse. These mice are an excellent model of autoimmune diabetes (type I diabetes) where islet-antigen reactive T cells infiltrate islets of Langerhans and kill islet cells, and/or initiate an inflammatory process that results in islet cell death (Anderson and Bluestone, 2005).

Figure 8:
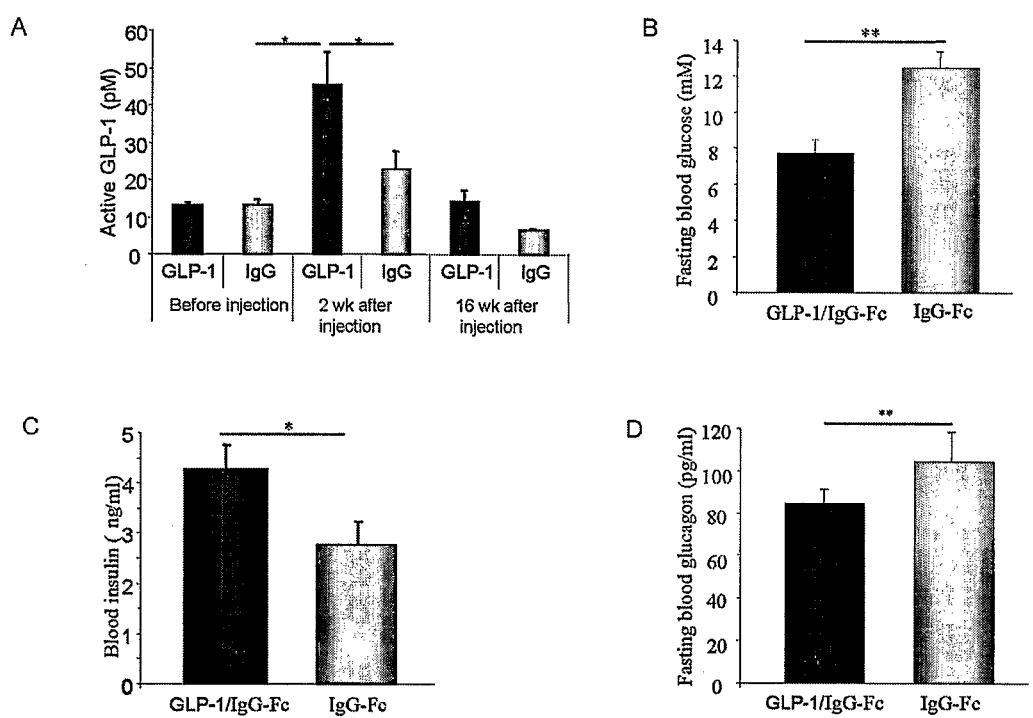
FIGS. 8A-D shows the effects of in vivo expression of GLP-1/IgG-Fc in type II diabetes model db/db mice. Db/db mice were intramuscularly injected with GLP-1/IgG-Fc and/ or Ex4/IgG-Fc or IgG-Fc vectors at 4 and/or 6 weeks of age local electroporation was applied. Serum was collected before injection and 2, 12 and 16 weeks after injection. Active GLP-1 levels were determined using a GLP-1 Elisa kit (8A). Fasting blood glucose levels in the two groups of mice were measured 12-week after first injection (n=5-6, p<0.001) (8B). Their blood insulin (8C) and glucagon (8D) levels were measured using RIA at 12 weeks after overnight starvation.

The administration of GLP-1/IgG-Fc (or Ex4/IgG-Fc) using a non-viral gene therapy approach was effective for the prevention and treatment of type I and type II diabetes. Non-viral vectors encoding any of the fusion proteins of the invention such as GLP-1/IgG-Fc molecule (or its DPPIV resistant fusion protein or Ex4/IgG-Fc molecule) are effective for treatment. Administration of the fusion proteins described by a gene transfer and a local Electroporation to db/db mice at age of 4 weeks. In all mice, a second injection was administered 2 weeks after the first injection, and the status of the development of diabetes were monitored. The db/db mouse genetically lacking leptin receptors, is a rodent model for type II diabetes (Leiter, FASEB 3. 1989; 3(11):2231-2241). As shown, age-matched db/db mice treated with a GLP-1/IgG-Fc via gene therapy approach exhibited normoglycemia at age of 16 weeks (12 weeks after injection), however, the control mice were hyperglycemic as determined by their fasting blood glucose (FBG) levels (FIG. 8). The GLP-1/IgG-Fc treated mice showed enhanced fasting insulin and reduced fasting glucagon (FIG. 8) levels. These results indicate that treatment with GLP-1/IgG-Fc prevented the onset of diabetes in the db/db mice. Protection against diabetes in db/db mice expressing GLP-1/IgG-Fc is in a good agreement with our previous findings that daily intraperitoneal (i.p.) Ex4 injection for two weeks prevented the development of diabetes in db/db mice (Wang and Brubaker, Diabetologia. 2002; 45(9): 1263-1273). The significance of our current therapy strategy is that two intramuscular injections of GLP-1/IgG-Fc vectors achieved similar effects as that by two weeks of daily i.p. injections of Ex4.

Figure 9:
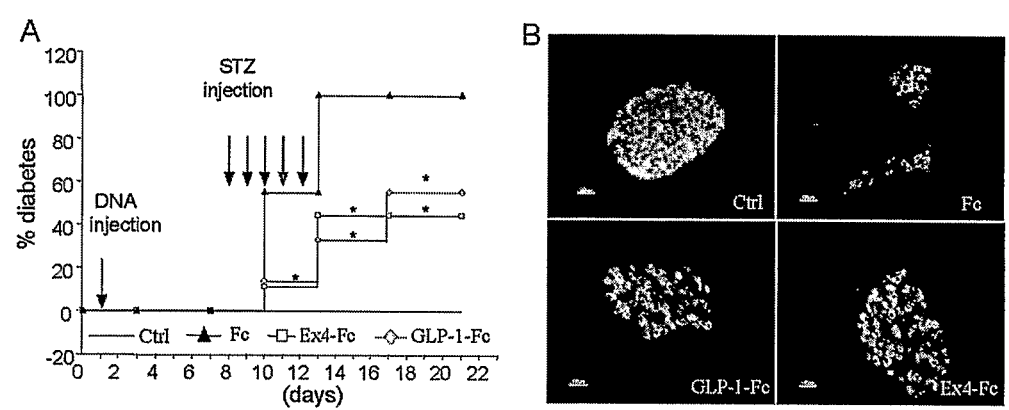
FIGS. 9A and 9B shows the effects of in vivo expression of GLP-1/IgG-Fc in insulin deficient type I diabetes model induced by streptozotocin. (9A) Vectors encoding GLP-1/ IgG-Fc, Ex4/IgG-Fc or IgG-Fc (50 μg/mice) were intramuscularly injected into CD1 mice and gene transfer was enhanced by a local electroporation. Seven days after DNA injection, the mice were received a booster injection and on the same day received a daily injection of STZ (55 mg/kg, i.p.) for consecutive 5 days. The blood glucose of the IgG-Fc-control mice rose markedly, reaching diabetic levels (≥17 mM) a few days after STZ injection, but the GLP-1/IgG-Fc (or Ex4/IgG-Fc) mice were protected and displayed a low incidence of overt diabetes. (9B) Pancreatic histology studies were performed in pancreatic sections prepared as previously reported (Wang et al., Mol Biol Cell. 1998; 9(11):3057-3069). The beta-cells were immunostained for overnight incubation at 4° C. using guinea pig anti-insulin IgG (1:1,000, Dako). After incubated with biotinylated mouse anti-guinea pig IgG (1:1, 100) for 60 min at room temperature, Cy3-conjugated avidin (1:1, 1000, Jackson Labs) was added for additional 45 min incubation. The images were taken using a Ziess Laser Scanning Microscope (Model 510). Total beta-cell mass per pancreas was determined as the product of the total cross-sectional insulin positive-beta-cell area/total tissue area and the weight of the pancreas before fixation. As shown the destruction of islet beta-cells occurred in all groups of mice treated with STZ, but the extent of damage was found to be lower in GLP-1/IgG-Fc (or Ex-4-IgG-Fc) mice. Infiltration of the islets by mononuclear cells (lymphocytes and/or macrophages) was observed in these mice (not shown). Interestingly, Ex4/IgG-Fc treatment yielded a result similar to GLP-1/IgG-Fc, even though Ex4/IgG-Fc is expected to resist DPPIV degradation. These findings indicate that expression of GLP-1/IgG-Fc (or Ex4/IgG-Fc) protected against the STZ-induced beta-cell damage in spite of the presence of islet inflammation (insulitis).
Figure 10:
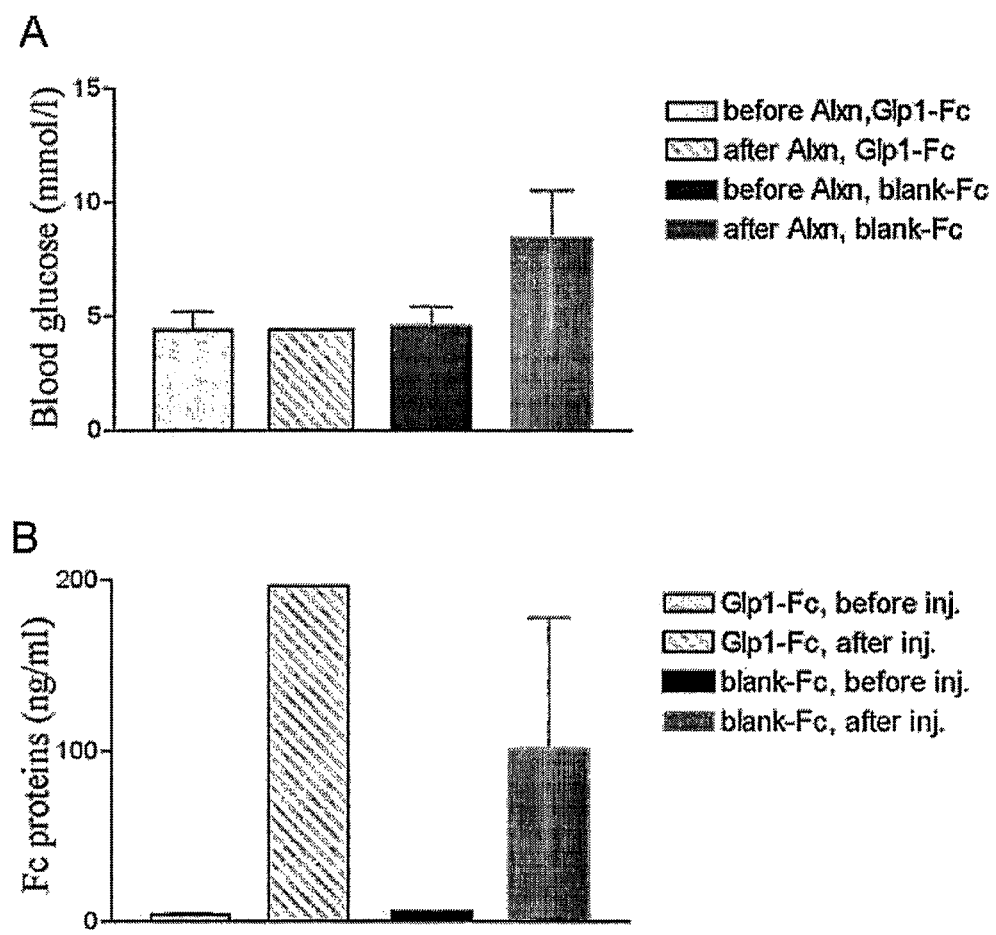
FIG. 10 shows the in vivo expression of GLP-1/IgG-Fc and its effect on blood glucose in pigs. GLP-1/IgG-Fc or control IgG-Fc vectors (4 mg/pig) were injected intramuscularly into male Yorkshire pigs (23 kg) followed by electroporation using the ADViSYS electroporator. To induce hyperglycemia, three days after the GLP-1/IgG-Fc vector injection, Alloxan monohydrate (Sigma/80 mg/kg) was administered in 25 ml saline intravenously under general Fluorothane-induced anesthesia. Initially, the acidic Alloxan solution was neutralized before injections. However, neutralized solution did not effectively cause hyperglycemia and thus subsequent injections were performed without neutralization, which resulted in moderate hyperglycemia in the blank IgG-Fc injected pigs, but not in the pigs injected with GLP-1/IgG-Fc vectors. The fasting blood glucose was tested twice a week in ketamine-sedated pigs when blood samples were withdrawn using a glucometer (A) and the expression of the Fc proteins was determined using ELISA (B).

Both GLP-1/IgG-Fc and Ex4/IgG-Fc were delivered into the CD1 mice through gene transfer and enhanced by local electroporation. Seven days after DNA injection, the mice were received a booster injection and meanwhile received STZ (55 mg/kg, i.p.) daily for consecutive 5 days. The blood glucose of the IgG-Fc-control mice rose markedly, reaching diabetic levels (≥17 mM) with a few days, but the GLP-1/IgG-Fc (or Ex4/IgG-Fc) mice were protected and displayed a low incidence of overt diabetes (FIG. 9). Pancreatic histological studies demonstrated that destruction of islet beta-cells occurred in both group mice, but the extent of damage was found to be lower in GLP-1/IgG-Fc (or Ex4/IgG-Fc) mice (FIG. 9), indicating beta-cell protective effect of GLP-1/IgG-Fc (or Ex4/IgG-Fc). Infiltration of the islets by mononuclear cells (lymphocytes and/or macrophages) was observed in both groups mice (not shown). Interestingly, Ex4/IgG-Fc treatment yielded a result similar to GLP-1/IgG-Fc, even though Ex4/IgG-Fc is expected to resist DPPIV degradation. These findings indicated that expression of GLP-1/IgG-Fc(or Ex4/IgG-Fc) protected against the STZ-induced beta-cell damage in spite of the presence of islet inflammation (insulitis). The treatment of GLP-1/IgG-Fc or Ex4/IgG-Fc protected streptozotocin-induced beta-cells damage most likely via increased beta-cell proliferation, neogenesis and decreased beta-cell apoptosis of which is in accord with our previous studies using GLP-1/Ex4 in these mice.

The GLP-1 derived molecule described in this report is the result of fusion of the GLP-1 and IgG-Fc cDNA sequences (FIG. 1). In an embodiment of the invention, the IgG subclass may be mouse $IgG_1$ or human $IgG_2$. Using human $IgG_2$ in the fusion protein of the invention has advantages over the use of another subclass of IgG, the $IgG_4$. $IgG_2$, unlike $IgG_4$, does not bind to Fc-gammaRI (the high affinity, activating Fc receptor that can bind monomeric IgG). Therefore, $IgG_2$ cannot deliver any activating signals, or promote any other effector function through the high affinity Fc receptor (Fc-gammRI). Furthermore, because of genetic differences in the population in Fc receptors (specifically the Fc-gammaRIIa activating receptor), $IgG_2$ can only act as an opsonin in 50% of people (because $IgG_4$ binds to Fc-gammaRI, it is an opsonin in all people). In people without $IgG_2$ opsonization, there will be a reduced chance that cells coated with $IgG_2$-Fc will be attacked and phagocytosed by macrophages or other phagocytic cells. Furthermore, in the 50% of people without opsonization due to polymorphism of the Fc-gammaRIIa receptor, $IgG_2$-Fc will also lack activating effects on effector cells and, therefore, the inhibitory effects mediated by the Fc-gammaRIIB receptor on some immune cells will be greater (compared to $IgG_4$). This means that genetic differences in Fc receptors will favour $IgG_2$-Fc over $IgG_4$-Fc in about 50% of people in terms of safety. Another advantage is that the transplacental transfer of $IgG_2$ in pregnant women will be less, reducing any risks for the fetus. This is a significant advantage for women of child bearing age (Kolar, G R and Capra, J D. Immunoglobulins: Structure and Function. In Fundamental Immunology (Ed. William E. Paul), Lippincott Willimans and Wilkins publishers, Philadelphia, 2003, pp. 47-68; Janeway Jr, C A, Travers, P, Walport M, Schlomchik M J (Editors). Immunobiology, Garland Science publishers, New York, 2005, pp. 387-391; and Roitt, R, Brostoff, J, Male, D (Editors). Immunology, 6th Edition, Mosby publishers, Edinburgh, 2001, pp. 73-78).

An IgG-Fc based drug provides a numbers of advantages. Since the IgG fusion molecules are produced as homodimers of 70 kilodaltons, they are not rapidly cleared by the kidneys, and they have a substantially longer half-life (Larrick and Fry, Hum Antibodies Hybridomas. 1991; 2(4):172-189; Weir et al., Biochem Soc Trans. 2002; 30(4):512-516). Thus, the larger GLP-1/IgG-Fc homodimeric fusion molecule will have increased circulating half-life compared to native GLP-1. The GLP-1/IgG-Fc fusion protein would have reduced susceptibility to degradation since such degrading enzymes have a preference for smaller peptides (Hupe-Sodmann et al., Regul Pept. 1995; 58(3):149-156). Furthermore, the dimeric GLP-1 is expected to increase the ligand avidity since homodimerized GLP-1 can potentially recruit additional GLP-1Rs and amplify intracellular signaling via preformed GPCR dimers/oligomers (George et al., Nat Rev Drug Discov. 2002; 1(10):808-820; Dupuis et al., Brain Res Mol Brain Res. 1999; 67(1):107-123). The cAMP and insulin secretion assays described herein suggest that the fusion proteins of the invention are able to activate GLP-1Rs in clonal INS-1 cells. The ability of the fusion protein to stimulate insulin secretion in INS-1 cells in a glucose-dependent manner further suggests that the GLP-1 fusion protein retains the biological function of the native GLP-1.

The in vivo effects of the GLP-1/IgG-Fc fusion protein on lowering blood glucose levels as demonstrated in db/db mice by an intramuscular gene transfer approach. This has the advantage of continuously releasing fusion protein into the circulation over a period of weeks. The circulating GLP-1 fusion proteins were detectable in the db/db mice two weeks after intramuscular injection of GLP-1/IgG-Fc vectors but not in the mice injected with control IgG-only plasmids. Interestingly, the significant fasting blood glucose lowering effects were only observed 12 weeks after the first injection. The reduced fasting blood glucose levels in the GLP-1/IgG-Fc expressing mice were associated with increased fasting insulin levels and decreased fasting glucagon levels suggesting that the normalization of the fasting blood glucose was contributed by enhanced insulin secretion and suppressed glucagon release.

The db/db mice are a severe type II diabetes model because of a deficiency in leptin signaling (Herberg and Coleman, Metabolism. 1977; 26(i):59-99; Chen et al., Cell. 1996; 84(3):491-495). Initially, the glucose levels in both the groups continued to rise perhaps as a result of progressive, unabated diabetes in the db/db mice. Normalization of blood glucose levels was only observed at 3 months post-injection. Most reports of muscle DNA injections suggest peak expression of plasmid after 1-2 weeks of injections. Our measurements of GLP-1 levels in the serum indicate an increase 2 weeks after injection (FIG. 8A). However, the translation of this increase into blood glucose normalization and an increase in fasting insulin and decrease in glucagon levels was observed much later. It is possible that the glucose normalization in this approach may be influenced more by the effect of the fusion proteins on beta-cell regeneration (beta-cell proliferation and neogenesis) and less by the immediate insulin sensitization effects commonly attributed to native GLP-1.

In addition, an effect of GLP-1/IgG-Fc on body weight was not seen which is seen in some cases of native GLP-1 treatment in rodent models (Turton et al., Nature. 1996; 379(6560):69-72). However, anorectic effects have not been observed in several GLP-1 analogues in spite of clear insulinotrophic glucose lowering effects (Kim et al., Diabetes. 2003; 52(3):751-759). Treatment with the long-lasting and potent GLP-1R agonist Ex4 improved fasting blood glucose in the db/db mice associated with enhanced beta-cells mass and function (Wang and Brubaker, Diabetologia. 2002; 45(9): 1263-1273). However, the body weight as well as the peripheral insulin sensitivities remained unchanged (Wang and Brubaker, Diabetologia. 2002; 45(9):1263-1273). These findings further support the notion that insulin resistance alone is not sufficient to trigger the onset of type II diabetes, which occurs only when the beta-cell dysfunction appears (Weyer et al., J Clin Invest. 1999; 104(6):787-794; Weyer et al., Diabetes. 1999; 48(11):2197-2203). The anorexic effects of GLP-1 have been linked to its action on multiple brain regions in the central nervous system (Schick et al., Am J Physiol Regul Integr Comp Physiol. 2003; 284(6):R1427-R1435). The ability of the GLP-1/IgG-Fc fusion protein to penetrate the blood-brain barriers needs to be further explored.

The transfer of naked plasmid DNA following needle injection occurs more readily in skeletal muscle than in most other tissues (Wolff et al., Biotechniques. 1991; 11(4):474-485; Wolff et al., Science. 1990; 247(4949 Pt 1):1465-1468). Moreover, transgene expression is generally much more prolonged than in other tissues, probably because striated myocytes are nondividing, long-lived cells. While gene transfection by naked DNA injection is not efficient, this is greatly improved (50 to 1000 fold) by in vivo Electroporation (Wells, Gene Ther. 2004; 11(18):1363-1369; Mir et al., Proc Natl Acad Sci USA. 1999; 96(8):4262-4267). Electric pulses are thought to increase DNA entry into cells by creating transient pores in the cell membrane, and by promoting DNA motility (electrophoretic effect). We apply low field strength (100-200 V/cm), relatively long (20-50 milliseconds) square-wave electric pulses, 6-8 times in quick succession. These low-voltage electrical pulses cause muscle damage, but it is usually mild and transient. In previous studies, the majority of surviving fibers expressed a reporter gene after vector delivery and electroporation. Two weeks after electroporation the muscles appeared grossly normal (Mathiesen, Gene Ther. 1999; 6(4):508-514).

Intramuscular delivery of plasmid vectors has proven to be an efficient and safe method of gene transfer when combined with in vivo electroporation. This method is versatile, and has been applied to the delivery of cytokines, peptide hormones, soluble receptors, as well as many membrane-bound or cytoplasmic proteins. Indeed, it is particularly useful for the systemic delivery of protein mediators, such as a GLP-1/IgG-Fc fusion protein. The IgG fusion approach has the advantage of a simple one-step procedure for the production of a GLP-1 fusion peptide on a laboratory scale. GLP-1 RIAs showed that the production efficiency is lower in a bacterial expression system than a mammalian expression system. This may be attributed to misfolded proteins in *E. Coli* compared to COS-7 cells, although the use of Rosetta gami 2 bacterial cells was intended to enhance properly folded and functional proteins, which is achieved by increasing the formation of disulfide bonds in the *E. coli* cytoplasm (Prinz et al., J Biol. Chem. 1997; 272(25):15661-15667) and providing rare codon tRNAs compensating for insufficient levels in the *E. coli* system (Kurland and Gallant, Curr Opin Biotechnol. 1996; 7(5):489-493).

Taken together the present invention is directed to a composition of GLP-1 (mouse or human as GLP-1 is identical in these species (Perfetti and Merkel, Eur J Endocrinol. 2000; 143(6):717-725; Holst, Gastroenterology. 1994; 107(6): 1848-1855)) to a IgG-Fc derivative (forming GLP-1/IgG-Fc) to increase half-life, improve in vivo activity and reduce immunogenicity. The bivalent GLP-1/IgG-Fc fusion protein exists in native conditions. The fusion proteins display a capacity to stimulate insulin secretion in a glucose-dependent manner and cAMP generation in INS-1 cells. In an embodiment of the invention, the GLP-1/IgG-Fc fusion protein may be delivered to a subject via a direct injection. In vivo studies using mouse models demonstrated that this composition may be delivered through a nonviral gene therapy approach, which results in long-term expression of the fusion protein. This proved protective against streptozotocin (STZ)-induced diabetes, a model of beta-cell injury and type I diabetes, and treatment of diabetes in db/db mice, a type II diabetes model. Lastly, the composition also proved protective against alloxan monohydrate induced hyperglycemia in pigs.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1

Plasmid Construction

A vector encoding a fusion protein consisting of the human GLP-1 (7-37) and mouse $IgG_1$-Fc using overlap PCR was constructed. The $IgG_1$-Fc region contains the $IgG_1$ constant heavy-chain (part of CH1, hinge, CH2 and CH3). An IgK secretion leader peptide sequence was fused with the GLP-1 sequence that directs the secretion of the synthesized peptide into the medium. The cDNA encoding the fusion protein hGHRH/hGLP-1 was chemically synthesized, ligated to a PCR-amplified cDNA fragment encoding human $IgG_2$ FC (hinge-ch2-ch3) and inserted into the NcoI and Hind III sites of the pAV0243 vector to generate GLP-1/hIgG-Fc/pAV0243. The secretable GLP-1/hIgG-Fc fusion protein contains the $IgG_2$ constant heavy-chain (hinge, CH2 and CH3). A GHRH secretion leader peptide sequence was fused with the GLP-1 sequence that directs the secretion of the synthesized peptide into the medium. This strategy ensured the generation of a GLP-1 fusion with an active histidine residue at the N-terminus of the fusion protein after cleavage of the secretion leader sequence peptide during the process of secretion. The schematic representation of the secreted GLP-1/IgG-Fc fusion proteins is shown in FIG. 1. This approach is expected to 1) circumvent the short circulating half-life of GLP-1 since Fc fusion proteins are secreted as homodimers that possess longer circulating half-life and higher efficacy due to higher ligand avidity (Ozmen et al., J. Immunol. 1993; 150(7):2698-2705; Kurschner et al., J. Immunol. 1992; 149(12):4096-4100; Kurschner et al., J Biol. Chem. 1992; 267(13):9354-9360); 2) enhance the peptide potency since most GPCR are pre-formed in dimers at the cell surface (George et al., Nat Rev Drug Discov. 2002; 1(10):808-820; Dupuis et al., Brain Res Mol Brain Res. 1999; 67(1):107-123); and 3) facilitate the purification, which can be achieved by one-step purification using Protein G sepharose (Jungbauer et al., J Chromatogr. 1989; 476:257-268).

Full length GLP-1 and mouse IgG-Fc cDNAs were amplified from GLP-1/PCR2.1 (kind gift from Dr. X Huang) and IgG plasmids using gene specific primers and overlap PCR. For the first overlap PCR, 5'-CCGGATATCGCCACCATG-GAGACAGACACACTCCTGCTATGGG-TACTGCTGCTCTGGGTTCCAGGTTC-CACTGGTGACCA-3' (SEQ ID NO:11) and 5'-TGCTGAAGGGACCTTTACCAGTG-3' (SEQ ID NO: 12) were used. The PCR products were used in a second overlap PCR to produce a contingent GLP-1/IgG-Fc cDNA. The amplification products were sub-cloned into the Bam HI and Eco RV sites of the vector. For the control vector that encodes IgG-Fc. IgG cDNA alone was amplified by PCR using 5'-CCGGATATCGCCACCATGGAGACAGACA- CACTCCTGCTATGGGTACTGCT-
GCTCTGGGTTCCAGGTTCCACTGGTGAC-
CCCAGCGAGACCGTCACC-3' (SEQ ID NO:13) and 5'-CGCGGATCCCTATCATTTACCAG-
GAGAGTGGGAGAGG-3' (SEQ ID NO:14) and cloned into the Bam HI and Eco RV sites of the vector.

The primers used for PCR-amplification of cDNA fragment encoding human IgG2 FC (hinge-ch2-ch3) were: 5'-AAGGATATCGATCGCAAATGTTGTGTC-
GAGTGCCCA-3' (SEQ ID NO:19) and 5'-CGTAAGCT-
TCATTTACCCGGAGACAGGGAGAG-3' (SEQ ID NO:20).

The vector contains a CMV immediate-early enhancer-promoter, a single eukaryotic transcription unit, and minimal rabbit beta globin polyadenylation and transcription termination sequences (Hartikka et al., Hum Gene Ther. 1996; 7(10): 1205-1217). The vector is a derivative of the VR1255 vector (Hartikka et al., Hum Gene Ther. 1996; 7(10):1205-1217), which has been modified by deleting the luciferase reporter gene and adding enzyme restriction sites. To permit secretion, the Igk-chain signal peptide sequence was introduced 5' to the GLP-1 or Ex4 sequence by PCR. To express GLP-1/IgG-Fc fusion proteins in bacteria, the fusion cDNA sequences were amplified by PCR from the plasmids and sub-cloned into the pET-28a (Novagen, EMD Bioscience, San Diego, Calif.) vector.

Example 2

Mammalian Expression of GLP-1/IgG-Fc Fusion Proteins

To assess the capacity of the vectors in terms of expression and secretion of the GLP-1/IgG-Fc fusion proteins, constructs were transiently transfected into COS-7 cells. Forty-eight hours after transfection, to evaluate the expression of the fusion constructs, total RNA from the transfected cells was prepared and expression was analyzed using RT-PCR. Transcripts for the GLP-1/IgG-Fc fusion constructs and IgG-Fc control constructs were detected using the gene specific primers (FIG. 2a). No transcripts were detected in non-transfected samples.

The lysates and conditioned medium from the transfected COS-7 cells were also analyzed for expression of the fusion proteins by Western blotting using anti-mouse antibodies. As shown in FIG. 2b, Fc fusion proteins were detected in both the medium and cell lysates. The fusion proteins migrated at 35 kDa, the size of the fusion protein monomers under the SDS-PAGE reducing conditions. Detection of the fusion proteins both in the conditioned media and the cell lysates shows that the fusion proteins were synthesized and secreted from the mammalian cells.

The identity of the GLP-1 fusion protein was further confirmed by a GLP-1 radioimmunoassay (RIA), which allows for detection of all forms of GLP-1. COS-7 cells were transiently transfected with increasing amounts of GLP-1/IgG-Fc/VRnew or Fc-only plasmids and media were collected 48 hours following transfection. The medium was used in GLP-1 RIAs to detect total GLP-1. While no GLP-1 was detected in medium from non-transfected or Fc-only/VRnew transfected COS-7 cells, GLP-1 was detected in a DNA-dose dependent manner in the medium collected from GLP-1-Fc/VRnew-transfected cells (FIG. 3). Up to 100 μmol of total GLP-1 was purified from 50 mL of COS-7 medium after transfection with 0.8 μg of DNA/$1.25 \times 10^5$ cells/ml.

Specifically, for mammalian expression, GLP-1/IgG-Fc or IgG-Fc cDNA was transfected into COS-7 cells using Lipofectamine-2000 (Invitrogen, Carlsbad, Calif.) according to manufacture's instructions. Briefly, cells grown in 6-well plates ($2.5 \times 10^5$ cells/well) were incubated with 4 μg of DNA IgG-Fc cDNAs using 10 μL of transfection agents in serum- and antibiotic-free DMEM (Invitrogen). Six hours after transfection, the cultures were placed in the complete culture medium. The medium and the cells were separately harvested 48 hours after transfection. For large-scale expression of GLP-1/IgG-Fc fusion proteins, COS-7 cells grown in 150 mm dishes were transfected with 80 μg of relevant cDNA using cationic transfection reagent, Poly(ethyleneimine) (PEI, 25 kDa). Briefly, DNA and PEI were separately diluted in 150 mM NaCl, mixed and incubated for 20 min. The DNA/PEI complexes were added to cells and incubated for 6 h in serum- and antibiotic-free medium. The medium was replaced with DMEM, 10% FBS and 1% P/S. This method produces ~85% transfection efficiency.

To establish stable COS-7 cells expressing GLP-1/IgG-Fc, the cells grown in 6-well plates ($2.5 \times 10^5$ cells/well) were transfected with 4 μg of linearized GLP-1/IgG-Fc or IgG-Fc. Twenty four hours after transfection, the cells were split and cultured in DMEM containing G418 (500 μg/mL) for selection of those cells that had stably integrated the recombinant plasmid into their genome. Culture medium was replaced every 3 days until colonies were formed. Individual colonies were isolated and expanded to stable cell lines and tissue culture supernatant from these cell lines grown in 24-well plates were tested for fusion protein using a rat GLP-1 RIA kit (see below). The cells capable of secreting fusion protein were chosen for further characterization.

Example 3

Purification of GLP-1/IgG-Fc Fusion Proteins from Mammalian Cell Culture Medium

For mini-purification, the medium collected from the transfected cells (typically 2.5 mL from each well of a 6-well plate) was added to 70 μL (packed volume) pre-washed Protein G Sepharose 4 Fast flow resin (Amersham-Pharmacia, Piscataway, N.J.) in buffer containing 100 mM Tris pH 8.0 and 150 mM NaCl. After overnight incubation at 4° C. and extensive washing with the Tris buffer, proteins were eluted directly from the resin by 30 μL of SDS sample buffer.

To acquire larger quantities of the fusion proteins, midi-scale purifications using Protein G sepharose columns employed 50 mL of conditioned culture media of COS-7 cells transfected with GLP-1/IgG-Fc-fusion vectors and grown in 15 cm dishes. Briefly, 50 mL of DMEM medium collected 48 hours post-transfection or from the cells stably expressing the fusion proteins were incubated with Protein G sepharose (1 mL packed volume, Amersham-Pharmacia). The incubations were performed overnight at 4° C. in the presence of 1% Triton X-100. After extensive washing with PBS containing 0.1% Triton X-100, and a final wash with 150 mM NaCl, proteins were eluted from the resin using 1 mL of 0.1 M glycine (pH 2.7). The elutions were immediately neutralized with Tris pH 9.0 buffer and the purified proteins were desalted using PD-10 columns (Amersham-Pharmacia) and eluted in PBS. As shown (FIG. 4A), a two-step elution approach allows removal of most of the fusion proteins from the sepharose column. A fraction of the samples were resolved by SDS PAGE and visualized by Coomassie Blue staining allowing for an estimation of production and purification yield (~6 μg/ml fusion protein in 2-day static culture when seeding at ~$1.25 \times 10^5$ cells/ml).

Example 4

Bacterial Expression of GLP-1/IgG-Fc Fusion Proteins

GLP-1/IgG-Fc fusion proteins were expressed in *E. Coli* cells. In order to compensate for the codon bias in *E. Coli*. BL21 cells, Rosetta gami 2 bacteria cells (Novagen, EMD biosciences, San Diego, Calif.) were used which allow enhanced disulphide bond formation and additionally harbor a plasmid for expression of seven rare tRNAs. After the cells were transformed with GLP-1/IgG-Fc/pET28a or IgG-Fc/pET28a vectors (Novagen), several individual colonies were selected and screened for optimal expression of the fusion proteins. For protein expression, a single colony of bacteria was used to inoculate 50 mL of 2×YT (with kanamycin) medium and grown overnight at 37° C. The culture was then diluted into fresh medium (1:50) and grown to $O.D._{600}$ 0.6. The expression was induced with 1 mM IPTG (EMD) for 3 hr. The bacteria were harvested and the pellet was stored at −80° C. for further processing. Briefly, to extract bacterial proteins, the pellets were resuspended in ice-cold PBS containing a protease inhibitor cocktail (Sigma, St. Louis, Mo.) and the cells were lysed by sonication. Proteins were solubilized using 1% Triton X-100 in PBS for 30 minutes. The centrifugation-clarified (12,000 g, 10 min) supernatant containing the fusion proteins was collected. The expressed proteins were purified using Protein G sepharose and analyzed using SDS-PAGE and Coomassie Blue staining (data not shown). About 120 µg of GLP-1/IgG-Fc and Fc-only fusion proteins were purified from 4 L of bacteria culture.

Figure 4B:
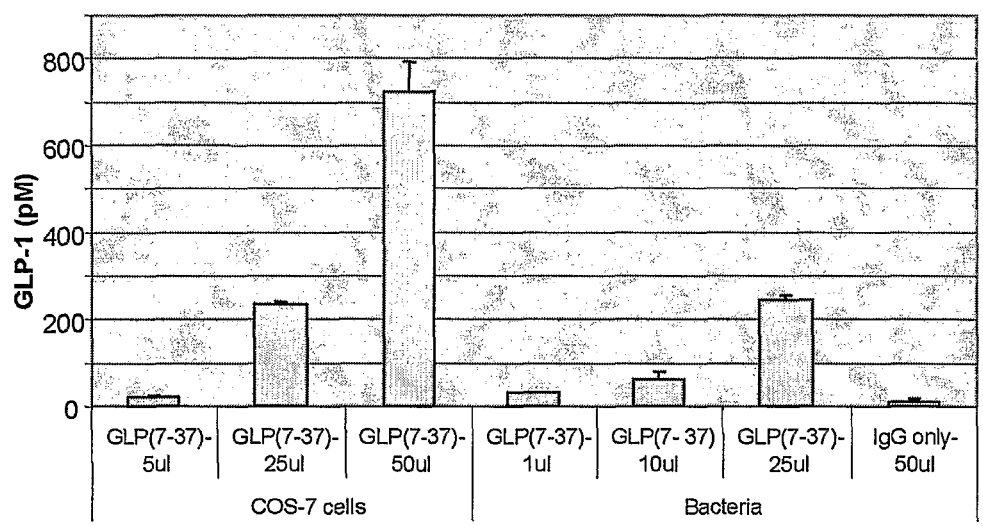
FIG. 4B shows GLP-1 expression in mammalian and bacterial cells. IgG-Fc fusion proteins expressed in COS-7 cells or bacteria (Rosetta gami 2) were purified using protein G sepharose. Varying amounts of purified protein were used for detection of GLP-1 protein using a total GLP-1 RIA kit.

Purified fusion proteins from mammalian and bacterial sources were further evaluated in a total GLP-1 RIA to confirm GLP-1 expression. A peptide dose-dependent increase in GLP-1 levels was observed with both mammalian and bacterial expressed GLP-1 fusion proteins. However, the expression levels of total GLP-1 were found to be lower in the bacteria than in the mammalian cells (FIG. 4B).

Example 5

Stable COS-7 Cells Secreting GLP-1/IgG-Fc Fusion Proteins

Figure 5:
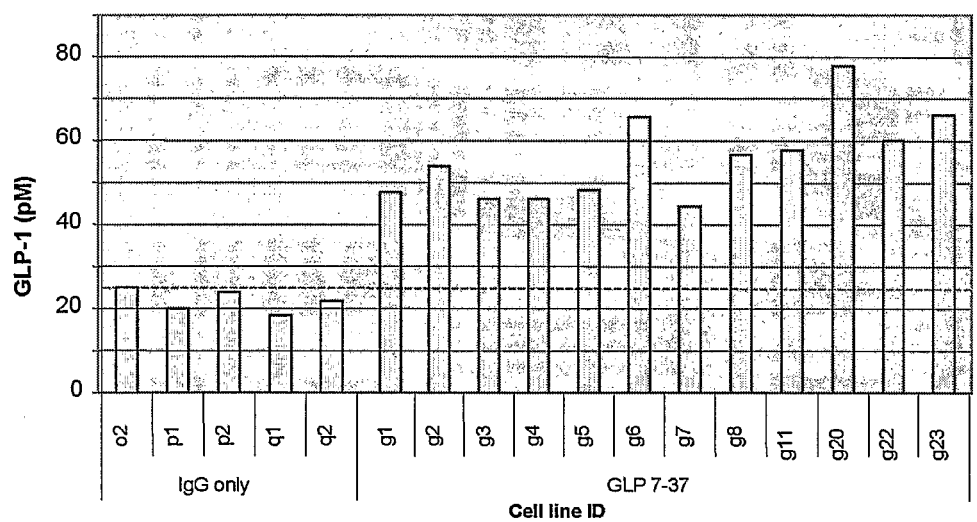
FIG. 5 shows the expression of GLP-1 in stably transfected COS-7 cells. COS-7 cells were transfected with GLP-1/IgG-Fc or IgG-Fc linearized plasmids and selected with 500 μg/mL of G418. After isolating potentially positive clones, the cells were grown in 12-well plates and medium was collected 48-h post-plating. The medium was used in total GLP-1 RIA assays to detect GLP-1 protein.

Stable COS-7 cells expressing GLP-1/IgG-Fc fusion proteins were established after selecting for G418 resistance and tested for GLP-1 secretion using a RIA. Total GLP-1 levels in the medium used to grow stable cells were used as a baseline to evaluate the expression levels in cells secreting GLP-1/IgG-Fc. As shown (FIG. 5), all the Fc-only stable cells secreted levels of GLP-1 lower than the medium baseline. We were able to isolate several clones expressing GLP-1/IgG-Fc fusion proteins which secreted GLP-1 at levels higher than the baseline were isolated (FIG. 5). However, the levels of secretion were low with less than a two-fold increase over baseline.

Example 6

In Vitro Characterization of GLP-1/IgG-Fc Fusion Proteins

Figure 6:
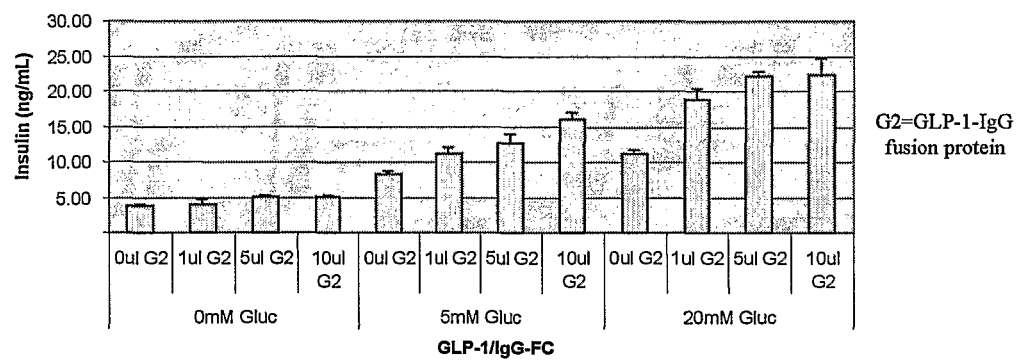
FIG. 6 shows the effect of GLP-1/IgG-Fc fusion treatment on insulin secretion in INS-1 cells. INS-1 cells were plated in 24-well plates and grown overnight. The cells were glucose- and serum-starved and treated with purified GLP-1/IgG fusion proteins for 1 h in KRB buffer with 0, 5 or 20 mM glucose. The medium was analyzed for insulin secretion using the insulin radioimmunoassay.

Native GLP-1 stimulates insulin secretion from beta-cells in a glucose-dependent manner (100). To evaluate whether the purified GLP-1/IgG-Fc fusion proteins from mammalian cells were functional, their effect on insulin secretion from clonal insulin-secreting INS-1 cells was determined. INS-1 cells were serum- and glucose-starved and were then treated with varying amounts of purified GLP-1/IgG-Fc fusion protein in the presence of 0, 5 or 20 mM glucose as indicated. As shown (FIG. 6), GLP-1/IgG-Fc did not stimulate insulin secretion from the beta-cells in the absence of glucose. However, in the presence of 5 mM or 20 mM glucose, the GLP-1/IgG-Fc stimulated insulin secretion from the beta-cells in a dose-dependent manner. The data indicates that the GLP-1/IgG-Fc fusion proteins are biologically active and are capable of stimulating insulin secretion in INS-1 cells in a glucose-dependent manner.

Example 7 cAMP Induction by GLP-1/IgG-Fc Fusion Peptides

Figure 7:
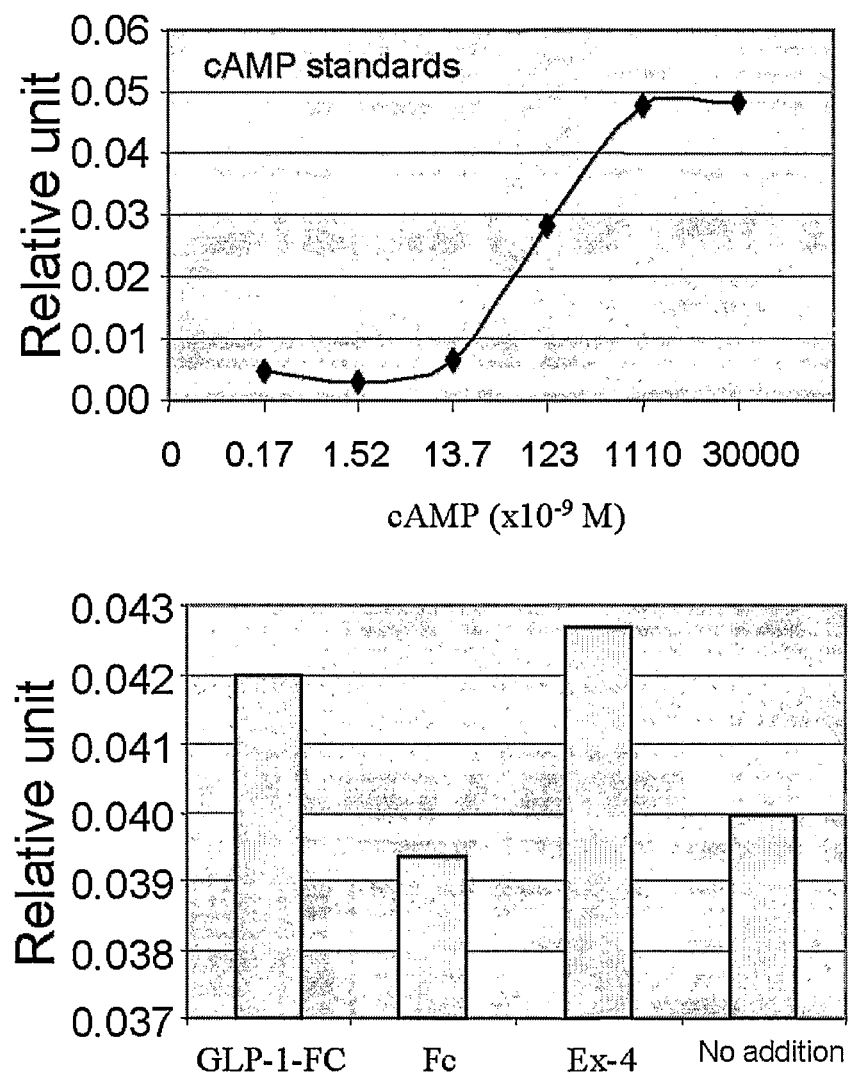
FIG. 7 is a graph demonstrating that GLP-1/IgG-FC exhibits similar efficacy as Ex-4 in generating cAMP in INS-1 cells. INS-1 cells were plated in 24-well plates and grown overnight. The cells were glucose- and serum-starved and treated with purified GLP-1/IgG-Fc fusion protein (IgG-Fc- and Ex4 as the negative and positive controls) for 10 min in serum-free RPMI medium with 0 or 5 mM glucose. cAMP levels in lyophilized aliquots of cell extracts were measured by radioimmunoassay.

In the absence of glucose, cAMP levels from the INS-1 cells treated with GLP-1/IgG-Fc (120 nM) were at basal levels (FIG. 7). However, in the presence of 5 mM glucose, the cAMP levels of GLP-1/IgG-Fc treated cells were significantly increased to a level that is comparable to that of cells treated with Ex4 (FIG. 7). The results indicate that GLP-1/IgG-Fc-stimulated cAMP generation in INS-1 cells is glucose concentration dependent.

Example 8

GLP-1/IgG-Fc Treatment Prevents the Onset of Diabetes in db/db Mice (Type II Diabetes Model)

4-week old female db/db mice (BKS.Cg-m+/+Lepr$^{db}$, stock number 000642) were purchased from Jackson Laboratories (Bar Harbor, Me., USA). Background age matched C57BLKS/J and CD1 control mice were obtained from Charles River Canada (Montreal, QC, Canada). Mice were housed under controlled light (12 hours light/12 hours dark) and temperature conditions, and had free access to food (normal rodent chow) and water. All procedures were conducted in accordance with the guidelines of the Canadian Council on Animal Care and were approved by the University of Toronto Animal Care Committee.

The diabetic db/db mice were treated by DNA injection/electroporation as previously described (Prud'homme and Chang, Gene Ther. 1999; 6(5):771-777) to enhance gene transfer. Briefly, anesthetized mice were injected in the tibialis anterior muscles with 50 µg of either GLP-1/IgG-Fc or IgG-Fc plasmids in PBS using a 27-gauge needle fitted with a plastic collar limiting muscle penetration to approximately 5 mm. The muscles were electroporated using electrodes fitted to a pair of calipers with three 100V square wave pulses (1 sec apart). In all mice, a second injection was administered 2 weeks after the first injection. The animals were monitored for bodyweight and fasting blood glucose weekly, and saphenous vein bleedings were collected prior to injection and 2 weeks and 12 weeks after the first injection for measurement of fasting insulin and glucagon levels. Blood was taken from the saphenous vein under fasting conditions at 4, 6 and 32 weeks after the DNA injection. The fasting blood glucose levels were measured using One Touch Basic glucose meter (Lifescan Canada, Burnaby, British Columbia, Canada), and the GLP-1, insulin and glucagon levels were measured as described below.

Expression of the GLP-1/IgG-Fc fusion protein was evaluated by measuring plasma levels of active GLP-1 using a GLP-1 Elisa kit (Linco). As shown, 2 weeks after the first injection the plasma GLP-1 levels were significantly elevated in mice injected with GLP-1/IgG-Fc compared to those mice injected with IgG-Fc vectors. The plasma GLP-1 levels returned to near basal levels 16 weeks after the first injection (FIG. 8A).

During the course of treatment, the bodyweight of mice in the two groups was not found to be significantly different (not shown). During the first month after injection, the fasting blood glucose levels were not significantly different between the two groups of mice (not shown). However, 12 weeks post-injection, the fasting blood glucose levels of the GLP-1/IgG-Fc producing mice were significantly lower ($P<0.001$) than the control mice (FIG. 8B). Furthermore, while the fasting insulin levels were found to be significantly elevated in the GLP-1/IgG-Fc producing mice compared with the IgG-Fc control mice ($P<0.05$) (FIG. 8C), the fasting glucagon levels were lower in the GLP-1 group mice compared to the control mice ($P<0.05$) (FIG. 8D). In vivo expression of GLP-1/IgG-Fc had glucose lowering effects in the db/db mice, likely due to the enhanced insulin secretion and the reduced basal glucagon release.

Example 9

GLP-1/IgG-Fc Treatment Prevents the Onset of Diabetes in STZ-Induced Insulin Deficient Mice (Type I Diabetes Model)

Recent studies suggest that the incretin function may be important in glycemic regulation in remission phase of type I diabetes (Dupre et al., J Clin Endocrinol Metab. 2004; 89(7): 3469-3473). To address the effectiveness of our GLP-1/IgG gene therapy in a model of beta islet-cell injury, its effects in streptozotocin (STZ)-induced diabetes in CD1 mice were studied. Vectors encoding either GLP-1/IgG-Fc, Ex4/IgG-Fc or IgG-Fc (50 μg/mice) were intramuscularly injected into CD1 mice and gene transfer was enhanced by local electroporation. Seven days after DNA injection, the mice received STZ (55 mg/kg, i.p.) daily for consecutive 5 days. The blood glucose of the IgG-Fc-control mice rose markedly, reaching diabetic levels (≥17 mM) with a few days, but the GLP-1/IgG-Fc (or Ex4/IgG-Fc) mice were protected and displayed a low incidence of overt diabetes (FIG. 9). Pancreatic histological studies demonstrated that destruction of islet beta-cells occurred in both group mice, but the extent of damage was found to be lower in GLP-1/IgG-Fc (or Ex4/IgG-Fc) mice (FIG. 9). Infiltration of the islets by mononuclear cells (lymphocytes and/or macrophages) was observed in both group mice (not shown). Interestingly, Ex4/IgG-Fc treatment yielded a result similar to GLP-1/IgG-Fc, even though Ex4/IgG-Fc is expected to resist DPP IV degradation. These findings indicate that expression of GLP-1/IgG-Fc (or Ex4/IgG-Fc) protected against the STZ-induced beta-cell damage in spite of the presence of islet inflammation (insulitis).

Example 10

In Vivo Expression of GLP1/IgG-Fc and its Effect on Blood Glucose in Pigs

GLP-1/IgG$_1$-Fc or control IgG$_1$-Fc vectors (4 mg/pig) were muscularly injected into male Yorkshire pigs (23 kg) followed by electroporation using ADViSYS electroporator. Three days after injection, Alloxan monohydrate (80 mg/kg, Sigma) was administered in 25 ml saline intravenously under general anesthesia by Fluorotan. Initially, the acidic Alloxan solution was neutralized before injections, Alloxan causes hyperglycemia. However, neutralized solution did not effectively cause hyperglycemia and thus subsequent injections were performed without neutralization which induced moderate hyperglycemia in the blank IgG-Fc injected pigs but not in the pigs injected with GLP-1/IgG-Fc vectors. The fasting blood glucose was tested twice a week in ketamine-sedated pigs when blood samples were withdrawn using a glucometer (A) and the expression of the Fc proteins were determined using ELISA (B).

Example 11

Detection of GLP-1/IgG-Fc Fusion Proteins by RT-PCR

Expression of IgG fusion transcripts were examined by using a one-step RT-PCR kit (Qiagen, Valencia, Calif.) using the gene specific primers. To detect GLP-1 fusion transcripts, 100 ng of total RNA from transfected COS-7 cells, and 0.6 μM of primers (5' CCGGATATCGCCACCATGGAGACA-GACACACTCCTGCTATGGTACTGCT-GCTCTGGGTTCCAGGTTCCACTGGTGAC-CATGCTGAAGGGACCTTTACCAGTG-3' (SEQ ID No: 15) and 5'-CGCGGATCCCTATCATTTACCAG-GAGAGTGGGAGAGG-3' (SEQ ID No: 16)) were used, while 5'-CCGGATATCGCCACCATGGAGACAGACA-CACTCCTGCTATGGGTACTGCT-GCTCTGGGTTCCAGGTTCCACTGGTGAC-CCCAGCGAGACCGTCACC-3' (SEQ ID No: 17) and 5'-CGCGGATCCCTATCATTTACCAG-GAGAGTGGGAGAGG-3' (SEQ ID No: 18) were used to detect IgG-Fc transcripts. The one-step RT-PCR conditions were 50° C. for 30 min, 95° C. for 15 min, 40 cycles of 94° C. for 30 sec, 55° C. for 30 sec and 72° C. for 60 sec followed by a 10 min extension at 72° C. The RT-PCR products were analyzed on a 1% agarose gel and visualized using ethidium bromide.

Example 12

Detection of GLP-1/IgG-Fc Fusion Proteins by SDS PAGE and/or Western Blotting

Mini-scaled purified fusion proteins (30 μL in SDS sample buffer) were resolved by 10% SDS-PAGE and transferred to a nitrocellulose membrane. The membrane was probed with anti-mouse antibody (1:5000, Amersham-Pharmacia) and visualized by ECL (Amersham-Pharmacia). An aliquot (30 μL) of Midi-scale purified fusion proteins were separated by 10% SDS-PAGE and visualized by Coomassie Blue staining.

Example 13

GLP-1 Secretion Assay

Using the total (all forms) GLP-1 RIA kit (Linco), GLP-1 levels were determined from medium (150 μL) collected from COS-7 cells transiently or stably expressing GLP-1/IgG-Fc or IgG-Fc fusion proteins or from the lysates of bacteria expressing the fusion proteins. For in vivo detection, GLP-1 levels in serum from db/db mice were determined using an active GLP-1 ELISA kit (Linco).

Example 14

Insulin and Glucagon Secretion Assays

INS-1 cells were plated in 24-well plates at a density of $2.5 \times 10^5$ cells/well in RPMI 1640 medium containing 10%

FBS. The following day the medium was replaced with fresh KRB buffer devoid of glucose for 2×30 min. The cells were then treated with 0, 5 or 20 mM glucose and various concentrations of purified GLP-1/IgG fusion proteins in KRB buffer for 1 hr. The insulin levels in conditioned KRB buffer (25 µL) were measured using a rat insulin RIA kit (Linco, St. Charles, Mo.). Plasma samples from db/db mice fasted for 16 h were measured for insulin and glucagon levels using a rat insulin RIA kit or rat glucagon RIA kit (Linco), according to the manufacturers instructions.

Measurement of cAMP:

INS-1 cells were plated at 62,500 cells/well in 24-well plates. The cells were serum starved in SF-RPMI containing 100 µM IBMX for 5 h prior to treatment the following day. The cells were subsequently incubated with purified GLP-1/IgG-Fc-fusion peptides (120 nM) or Ex4 (100 nM) for 10 min in 450 µL of SF—RPMI medium. The assay was terminated by the addition of 1 mL of ice-cold ethanol. The extracts were incubated at −20° C. for 3 h to overnight following which 200 µL of the extracts were aliquoted and lyophilized. The lyophilized extracts were resuspended in 50 µL of sodium acetate assay buffer and used in cAMP RIAs (Biomedical Technologies, Stoughton, Mass.).

Statistical Analysis.

All data are presented as mean±SEM. Statistic analysis was performed using Student's t-test or analysis of variance (ANOVA) with 'n−1' post hoc custom hypotheses tests, as appropriate, on SAS software (Statistical Analysis Systems, Cary, N.C.). Significance was assumed at $p<0.05$.

Example 15

Sample Protocols for Testing Fusion Proteins

Beta-Cell Mass Analysis:

Pancreatic sections (4 mm) were processed as previously described (Finegood et al., Diabetes. 2001; 50(5):1021-1029). Briefly, following dewaxing, dehydration and antigen retrieval (by boiling in citrate buffer), sections were incubated overnight at 4° C. with guinea pig anti-insulin antibody (Dako Diagnostics, Mississauga, ON, Canada). The samples were then incubated for 1 h with biotinylated anti-guinea pig antibody (Vector Laboratories, Burlington, ON, Canada), and subsequently treated for 1 h with avidin/biotin complex (Vectastain Elite ABC Kit; Vector Laboratories, Burlingame, Calif.). Sections were then stained with 3,3'-diaminobenzidine tetrahydrochloride (DAB; Sigma-Aldrich) for 10 min. After DAB staining, the sections are washed with tap water and counterstained with hematoxylin. Beta-cell mass from the insulin antibody-stained sections is measured using a Nikon (ECLIPSE-E1000) microscope connected to a video camera equipped with a color monitor and ImagePlus software, and the cross-sectional area occupied by all of the beta-cells and the cross-sectional area of all pancreatic tissue was quantified. Total beta-cell area and total pancreas mass for each animal were calculated as the sum of the determinations from each of the 8-10 segments of pancreas. A total of 1000-1500 beta-cells were counted per pancreas. Total beta-cell mass per pancreas was determined as the product of the total cross-sectional beta-cell area/total tissue area and the weight of the pancreas before fixation.

Receptor Binding Assay:

The composition of the invention was iodinated by a classical Chloramines-T method (HUNTER and GREENWOOD, Nature. 1962; 194:495-496). The receptor binding assay is performed as described previously (Wang et al., Cell Physiol Biochem. 1998; 8(6):304-313): isolated islet cells and insulin secreting cells were suspended in PBS and centrifuged at 600 g for 10 min, and the cell pellets were resuspended in aliquots of PBS. The binding of the iodinated composition of the invention to the intact cells was carried out in 7×35 mm polystyrene tubes at 4° C. in 300 ml assay buffer (PBS containing 0.2% BSA) with the labeled compound (20,000 cpm) in the presence or absence of unlabelled composition of the invention. After 4.5 hours of incubation, when the assay system reaches an equilibrium state, cold PBS was added, and the samples were centrifuged for 10 min at 600 g at 4° C. The supernatant was discarded. After washing the cell pellets with cold PBS, the radioactivity was measured in a gamma counter.

cAMP Determination:

cAMP determination is a method that can evaluate the G-protein coupled receptor (GPCR) activation (Lee et al., Biochim Biophys Acta. 2000; 1490(3):311-323). Intracellular cAMP levels were determined in isolated islet cells or cultured insulin-secreting cells cultured in 35 mm² dishes. They were preincubated in the buffer containing 130 mM NaCl, 5 mM KCl, 1 mM sodium phosphate, 1 mM MgSO4, 2 mM $CaCl_2$, 20 mM HEPES buffer (pH 7.4), 6 mm glucose, and 0.1% BSA (RIA grade, Sigma) for 1 h. The PKA inhibitors were added for 20 min, and isobutyl methylxanthine (100 µM) for 10 min before addition of the compound for 20 min. Cells were washed three times in ice-cold PBS, cAMP extracted with hydrochloric acid (0.1M, 300 µl) and measured as per the cAMP RIAs (Biomedical Technologies, Stoughton, Mass.).

PI 3-Kinase Activity Assay:

PI3-kinase is upstream of Akt (Wang et al., Mol Cell Biol. 1999; 19(6):4008-4018). Whole cell lysates were obtained from isolated islet cells and insulin-secreting cell line (eg INS-1 cells and beta TC cells) pre-treated with the composition of the invention for 20 min, and PI 3-kinase was immunoprecipitated using an antibody against the p85-regulatory subunit of PI 3-kinase (Santa Cruz Biotechnology). Activity was detected and quantified by measuring the formation of [$^{32}$P]PI 3-phosphate (Wang et al., Biochem J. 1998; 331(Pt 3):917-928). Briefly, after overnight incubation with the antibody-coated beads, the bound protein was washed three times with buffer I (PBS containing 1% Nonidet P-40 and 100 µM $Na_3VO_4$), three times with buffer II (100 mM Tris-HCl (pH 7.5), 500 mM LiCl, and 100 µM $Na_3VO_4$), and finally three times with buffer III (Tris-HCl (pH 7.5), 100 mM NaCl, 1 mM EDTA and 100 µM $Na_3VO_4$). After washing, immunoprecipitates are resuspended in 50 µl buffer III with the addition of 10 µl 100 mM $MgCl_2$ and 10 µl PI (2 µg/ml). The samples sat at room temperature for 5 min before the addition of 10 µl ATP (ATP 440 µM with 30 µCi/10 µl [$^{32}$P]ATP). The samples were then shaken at room temperature for 10 min. The reaction was stopped by the addition of 20 µl 8 N HCl and 160 µl chloroform-methanol (1:1). The lipids were extracted by standard methods, dried down, resuspended in 20 µl chloroform-methanol (1:1), were separated on thin layer silica gel plates (pretreated with 10% w/v potassium oxalate) in a solvent system of chloroform-methanol-water-$NH_4OH$ (60:47:11:2.2, vol/vol/vol/vol). Incorporation of $^{32}$P into PI 3-phosphate is detected by autoradiography, and activity was quantified using a Molecular Dynamics PhosphorImager System (Sunnyvale, Calif.).

Apoptosis Assay:

After treatment with the composition of the invention (0.5 to 24 hours), the apoptotic rate of isolated islet cells and/or insulin-secreting cell line (eg INS-1 cells and beta TC cells) was determined using APOPercentage Assay Kit (Biocolor Ltd. Ireland) according to manufacturers instructions. From the in vivo animal models, pancreas sections were obtained from subjects treated with or without the composition of the invention were double immunostained for insulin, as described above, and for fragmented DNA by Tunel assay, which detects fragmented nuclei characteristic of apoptotic cells. Tunel staining was performed using ApopTag Kit (Intergen, Purchas, N.Y.) according to manufacture's instruction. The islet tissue was identified as a red field for insulin staining (chromagen: New Fuchsin Substrate, DAKO), and apoptotic cells were identified by dark brown staining of nuclei (chromagen: 3,3'-Diaminobenzidine, Sigma). The results are expressed as the percentage of Tunel+ beta-cells.

Akt Kinase Assays:

After treatment with the composition of the invention for 10 min, whole cell lysates were obtained from isolated islet cells and insulin-secreting cell line (eg INS-1 cells and beta TC cells), using lysis buffer containing 50 mM HEPES (pH 7.6), 150 mM NaCl, 10% (vol/vol) glycerol, 1% (vol/vol) Triton X-100, 30 mM sodium pyrophosphate, 10 mM NaF, 1 mM EDTA, 1 mM phenylmethylsulfonyl fluoride, 1 mM benzamidine, 1 mM $Na_3VO_4$, 1 mM dithiothreitol [DTT], and 100 nM okadaic acid (Wang et al., Mol Cell Biol. 1999; 19(6):4008-4018). Akt antibody is precoupled (16 hours) to a mixture of protein A- and protein G-Sepharose beads. These antibody-bead complexes are washed twice with phosphate-buffered saline (PBS) and once with lysis buffer (4° C.). Akt is immunoprecipitated by incubating 200 µg of total cellular protein with the anti-Akt-bead complexes for 2 to 3 h with constant rotation (4° C.). Akt immunocomplexes were washed four times with 1 ml of wash buffer (25 mM HEPES [pH 7.8], 100/0 [vol/vol] glycerol, 10/0 [vol/vol] Triton X-100, 0.1% [wt/vol] bovine serum albumin, 1 M NaCl, 1 mM DTT, 1 mM phenylmethylsulfonyl fluoride, 1 mM microcystin, and 100 nM okadaic acid) and twice with 1 ml of kinase buffer (50 mM Tris-HCl [pH 7.5], 10 mM $MgCl_2$, and 1 mM DTT). The immunocomplexes were incubated with constant agitation for 30 minutes at 30° C. with 30 µL of reaction mixture (kinase buffer containing 5 µM ATP, 2 µCi of [$\gamma$-$^{32}$P]ATP, and 100 µM Crosstide). Following the reaction, 30 µl of the supernatant was transferred onto Whatman p81 filter paper and washed four times for 10 minutes each time with 3 ml of 175 mM phosphoric acid and once with distilled water for 5 min. The filters were air dried and then subjected to liquid scintillation counting.

MAP Kinase Assay:

After 20 min treatment with the composition of the invention, beta-cells were labeled with 1.25 microcurie $^{32}$Pi/group (NEN Life Science Products, Boston, Mass.) in phosphate-free RPMI medium without serum for 3 h at 37° C. The cells were harvested and placed in RPMI with 100 ng/ml LBP (PS-binding protein) and treated with the compositions of the invention for 30 min. After the incubation with the composition of the invention, the cells were stimulated with LPS for 15 min at 37° C. The cells were harvested, resuspended in lysis buffer (1% Nonidet P-40, 1% sodium deoxycholate, 0.1% SDS, 0.15 M NaCl, 0.01 M Na3PO4 (pH 7.2), 2 mM $Na_3VO_4$, 1 µM okadaic acid, 100 µg/ml PMSF, 50 µg/ml aprotinin, 10 µg/ml leupeptin, and 50 µg/ml pepstatin, all from Boehringer Mannheim), and sonicated. MEK was immunoprecipitated from the lysate, and the sample separated on a 10% SDS-PAGE discontinuous gel, and immunoblotting was performed using anti-phosphor-MEK antibody (Oncogene Research Products, San Diego, Calif.).

Other assays (as well as variations of the above assay) will be apparent from the description of this invention and techniques such as those disclosed in U.S. Pat. Nos. 5,851,788, 5,736,337 and 5,767,075 which are incorporated by reference in their entirety. For example, the composition of the invention may be incubated with beta-cells to determine if the composition of the invention inhibits caspase-3 by Western blot analysis using specific antibody against phosphor-caspase-3 (Oncogene Research Products, San Diego, Calif.).

Table One: Sequences of GLP-1, Ex4, Mouse $IgG_1$-Fc, IgK, Human $IgG_2$, Human GHRH Leader Sequence, PCR Primers and Sequences of Some Compounds Optionally Used in the Assays Described in this Application are Provided:

```
GLP-1
                                                    (SEQ ID NO: 1)
HAEGTFTSDV SSYLEGQAAK EFIAWLVKGR-NH2

Ex4
                                                    (SEQ ID NO: 2)
HGEGTFTSDL SKQMEEEAVR LFIEWLKNGG PSSGAPPPS-NH2

IgG1-Fc
                                                    (SEQ ID NO: 3)
PSETVTCNVA HPASSTKVDK KIVPRDCGCK PCICTVPEVS

SVFIFPPKPK DVLTITLTPK VTCVVVDISK DDPEVQFSWF

VDDVEVHTAQ TQPREEQFNS TFRSVSELPI MHQDWLNGKE

FKCRVNSAAF PAPIEKTISK TKGRPKAPQV YTIPPPKEQM

AKDKVSLTCM ITDFFPEDIT VEWQWNGQPA ENYKNTQPIM

NTNGSYFVYS KLNVQKSNWE AGNTFTCSVL HEGLHNHHTE

KSLSHSPGK

IgK
                                                    (SEQ ID NO: 4)
METDTLLLWV LLLWVPGSTG D
```

Human Akt/Protein Kinase B:

```
                                                    (SEQ ID NO: 5)
  1 mkterprpnt fiirclqwtt viertfhvet peereewtta iqtvadglkk qeeeemdfrs 61 gspsdnsgae emevslakpk hrvtmnefey lkllgkgtfg kvilvkekat ayyamkilkk 121 evivakdeva htltenrvqq nsrhpfltrl kysfqthdrl cfvmeyangg elffhlsrer 181 vfaedrarfy gaeivsaldy lhseknvvyr dlklenlmld kdghikitdf glckegikdg 241 atmktfcgtp eylapevled ndygravdww glgvvmyemm cgrlpfynqd heklfelilm 301 eeirfprtlg peaksllsgl lkkdpkqrlg ggsedakeim qhrfftgivw qhvyekklsp 361 pfkpqvtset dtryfdeeft aqmititppd qddsmecvds errphfpqfs yspsata
```

Human MAP Kinase:

(SEQ ID NO: 6)

```
  1 msdskcdsqf ysvqvadstf tvlkryqqlk pigsgaqgiv caafdtvigi nvavkklsrp
 61 fqnqthakra yrelvllkcv nhkniisllrn vftpqktlee fqdvylvmei mdanlcqvih
121 meldhermsy llyqmicgik hlhsagiihr dlkpsnivvk sdctlkildf glartactnf
181 mmtpyvvtry yrapeviigm gykenvdiws vgcimgelvk gcvifqgtdh idqwnkvieq
241 lgtpsaefmk klqptvrnyv enrpkypgik feelfpdwif pseserdkik tsqardllsk
301 mlvidpdkri svdealrhpy itvwydpaea eapppqiyda qleerehaie ewkeliykev
361 mdweerskng vvkdqpsdaa vssnatpsqs ssindissms teqtlasdtd ssldastgpl
421 egcr
```

Human Caspase-3:

(SEQ ID NO: 7)

```
  1 mentensvds ksiknlepki ihgsesmdsg mswdtgykmd ypemglciii nnknfhkstg
 61 mtsrsgtdvd aanlretfrn lkyevrnknd ltreelveim rdvskedhsk rssfvcvlls
121 hgeegiifgt ngpvdlkkit nffrgdrcrs ltgkpklfii qacrgteldc gietdsgvdd
181 dmachkipvd adflyaysta pgyyswrnsk dgswfiqslc amlkqyadkl efmhiltrvn
241 rkvatefesf sfdatfhakk qipcivsmlt kelyfyhl
```

Human IgG₂-Fc (788-1689)-cDNA:

(SEQ ID NO: 8)

```
 788 gag cgcaaatgtt gtgtcgagtg cccaccgtgc ccaggtaagc cagcccaggc
 841 ctcgccctcc agctcaaggc gggacaggtg cctagagta gcctgcatcc agggacaggc
 901 cccagctggg tgctgacacg tccacctcca tctcttcctc agcaccacct gtggcaggac
 961 cgtcagtctt cctcttcccc ccaaaaccca aggacaccct catg atctcc cggaccctg
1021 aggtcacgtg cgtggtggtg gacgtgagcc acgaagaccc cgaggtccag ttcaactggt
1081 acgtggacgg cgtggaggtg cataatgcca agacaaagcc acgggaggag cagttcaaca
1141 gcacgttccg tgtggtcagc gtcctcaccg ttgtgcacca ggactggctg aacggcaagg
1201 agtacaagtg caaggtctcc aacaaaggcc tcccagcccc catcgagaaa accatctcca
1261 aaaccaaagg tgggacccgc ggggtatgag ggccacatgg acagaggccg gctcggccca
1321 ccctctgccc tgggagtgac cgctgtgcca acctctgtcc ctacagggca gccccgagaa
1381 ccacaggtgt acaccctgcc cccatcccgg gaggagatga ccaagaacca ggtcagcctg
1441 acctgcctgg tcaaaggctt ctaccccagc gacatcgccg tggagtggga gagcaatggg
1501 cagccggaga acaactacaa gaccacacct cccatgctgg actccgacgg ctccttcttc
1561 ctctacagca agctcaccgt ggacaagagc aggtggcagc aggggaacgt cttctcatgc
1621 tccgtgatgc atgaggctct gcacaaccac tacacgcaga agagcctctc cctgtctccg
1681 ggtaaatga
```

Human IgG₂-Fc (788-1689)-Amino Acid:

(SEQ ID NO: 9)

ERKCCVECPPCPAPPVAGPSVFLFPPKPKDTLMISRTPEVTCVVVDVSHE
DPEVQFNWYVDGVEVHNAKTKPREEQFNSTFRVVSVLTVVHQDWLNGKEY
KCKVSNKGLPAPIEKTISKTKGQPREPQVYTLPPSREEMTKNQVSLTCLV
KGFYPSDIAVEWESNGQPENNYKTTPPMLDSDGSFFLYSKLTVDKSRWQ
QGNVFSCSVMHEALHNHYTQKSLSLSPGK

Human Growth Hormone Releasing Hormone (GHRH) Leader Sequence:

(SEQ ID No: 10)
gtg ctc tgg gtg ttc ttc ttt gtg atc ctc acc ctc agc aac agc tcc cac tgc tcc PCR Primers:

(SEQ ID No: 11)
5'-CCGGATATCGCCACCATGGAGACAGACACACTCCTGCTATGGGTACTGCTGCTCTGGGTTCCAGGTTCCACTGGTGACCA-3'

(SEQ ID No: 12)
5'-TGCTGAAGGGACCTTTACCAGTG-3'

(SEQ ID No: 13)
5'-CCGGATATCGCCACCATGGAGACAGACACACTCCTGCTATGGGTACTGCTGCTCTGGGTTCCAGGTTCCACTGGTGACCCCAGCGAGACCGTCACC-3'

(SEQ ID No: 14)
5'-CGCGGATCCCTATCATTTACCAGGAGAGTGGGAGAGG-3'

(SEQ ID No: 15)
5'CCGGATATCGCCACCATGGAGACAGACACACTCCTGCTATGGGTACTGCTGCTCTGGGTTCCAGGTTCCACTGGTGACCATGCTGAAGGGACCTTTACCAGTG-3'

(SEQ ID No: 16)
5'-CGCGGATCCCTATCATTTACCAGGAGAGTGGGAGAGG-3'

(SEQ ID No: 17)
5'-CCGGATATCGCCACCATGGAGACAGACACACTCCTGCTATGGGTACTGCTGCTCTGGGTTCCAGGTTCCACTGGTGACCCCAGCGAGACCGTCACC-3'

(SEQ ID No: 18)
5'-CGCGGATCCCTATCATTTACCAGGAGAGTGGGAGAGG-3'

(SEQ ID No: 19)
5'-AAGGATATCGATCGCAAATGTTGTGTCGAGTGCCCA-3'

(SEQ ID No: 20)
5'-CGTAAGCTTCATTTACCCGGAGACAGGGAGAG-3'

---

The invention claimed is:

1. A pharmaceutical composition comprising a heterologous fusion protein comprising: a GLP-1 polypeptide selected from GLP-1 (7-37), GLP-1 (7-36) amide, and DPPIV resistant GLP-1, fused to a human IgG2 heavy chain constant region (Fc), and a leading sequence, wherein the leading sequence directs secretion of the synthesized fusion protein and wherein said human IgG2 Fc comprises SEQ ID NO:9.

2. The pharmaceutical composition of claim 1, wherein cleavage of the leading sequence generates a fusion protein with a histidine residue at the N-terminus of the fusion protein.

3. The pharmaceutical composition of claim 1, wherein the leading sequence comprises an IgK secretion leader peptide sequence, comprising SEQ ID NO:4; or a GHRH secretion leader peptide sequence, encoded by SEQ ID NO:10.

4. A pharmaceutical composition comprising a heterologous fusion protein comprising a GLP-1 polypeptide selected from GLP-1 (7-37), GLP-1 (7-36) amide, and DPPIV resistant GLP-1, fused to a human IgG2 heavy chain constant region (Fc), wherein said human IgG2 Fc comprises SEQ ID NO:9.

5. The pharmaceutical composition of claim 4, wherein said DPPIV resistant GLP-1 is GLP-1A8G.

6. The pharmaceutical composition of claim 4, wherein said fragment of GLP-1 comprises at least 29 amino acids and is GLP-1(7-37) or GLP-1(7-36) amide.

* * * * *

UNITED STATES PATENT AND TRADEMARK OFFICE
CERTIFICATE OF CORRECTION

PATENT NO. : 8,658,174 B2  Page 1 of 1
APPLICATION NO. : 11/996776
DATED : February 25, 2014
INVENTOR(S) : Wang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1527 days.

Signed and Sealed this

Twenty-ninth Day of September, 2015

Michelle K. Lee
*Director of the United States Patent and Trademark Office*